(12) United States Patent
Fan et al.

(10) Patent No.: US 9,336,592 B2
(45) Date of Patent: May 10, 2016

(54) METHOD AND APPARATUS FOR DETERMINING TUMOR SHIFT DURING SURGERY USING A STEREO-OPTICAL THREE-DIMENSIONAL SURFACE-MAPPING SYSTEM

(71) Applicant: The Trustees of Dartmouth College, Hanover, NH (US)

(72) Inventors: Xiaoyao Fan, Lebanon, NH (US); David W. Roberts, Lyme, NH (US); Keith D. Paulsen, Hanover, NH (US); Songbai Ji, Lebanon, NH (US); Alex Hartov, Enfield, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 14/375,311

(22) PCT Filed: Feb. 1, 2013

(86) PCT No.: PCT/US2013/024400
§ 371 (c)(1),
(2) Date: Jul. 29, 2014

(87) PCT Pub. No.: WO2013/116694
PCT Pub. Date: Aug. 8, 2013

(65) Prior Publication Data
US 2014/0369584 A1 Dec. 18, 2014

Related U.S. Application Data

(63) Continuation-in-part of application No. PCT/US2013/020352, filed on Jan. 4, 2013.

(60) Provisional application No. 61/594,862, filed on Feb. 3, 2012.

(51) Int. Cl.
*G06K 9/00* (2006.01)
*G06T 7/00* (2006.01)
(Continued)

(52) U.S. Cl.
CPC .............. *G06T 7/0012* (2013.01); *A61B 5/1077* (2013.01); *A61B 5/1079* (2013.01);
(Continued)

(58) Field of Classification Search
None
See application file for complete search history.

(56) References Cited

U.S. PATENT DOCUMENTS

| 5,109,276 A | 4/1992 | Nudelman et al. |
| 6,175,759 B1 | 1/2001 | Chan et al. |

(Continued)

FOREIGN PATENT DOCUMENTS

| JP | 2006195240 A | 7/2006 |
| WO | 2005089637 A2 | 9/2005 |

(Continued)

OTHER PUBLICATIONS

PCT Application PCT/US2009/066839 International Search Report and Written Opinion dated Jun. 25, 2010, 11 pages.
(Continued)

*Primary Examiner* — Oneal R Mistry
(74) *Attorney, Agent, or Firm* — Lathrop & Gage LLP

(57) ABSTRACT

A system and method for determining intraoperative locations of a lesion in tissue from lesion locations determined in preoperative imaging includes determining three dimensional locations of surface features of the organ in the preoperative images. A preoperative surface map is extracted from stereo images annotated with surface features from preoperative images. An intraoperative surface map of the organ is extracted from stereo images, and surface features are identified in the stereo images corresponding to surface features annotated into the preoperative surface map. Three dimensional displacements of the surface features are determined and used to constrain a computer model of deformation of the organ. In embodiments, the model of deformation is adapted or constrained to model locations and dimensions of surgical cavities using an optical flow method and/or locations of surgical instruments in the organ. The model of deformation is used to determine intraoperative locations for the lesion.

18 Claims, 11 Drawing Sheets

(51) Int. Cl.

| | | |
|---|---|---|
| *G06T 17/00* | (2006.01) | |
| *A61B 6/00* | (2006.01) | |
| *A61B 5/00* | (2006.01) | |
| *A61B 5/107* | (2006.01) | |
| *G06K 9/60* | (2006.01) | |
| *G06T 19/20* | (2011.01) | |
| *A61B 5/055* | (2006.01) | |
| *A61B 19/00* | (2006.01) | |
| *A61B 8/08* | (2006.01) | |

(52) U.S. Cl.
CPC ............... *A61B5/7425* (2013.01); *A61B 6/501* (2013.01); *A61B 6/5247* (2013.01); *A61B 19/50* (2013.01); *A61B 19/5244* (2013.01); *G06K 9/60* (2013.01); *G06T 7/0028* (2013.01); *G06T 17/00* (2013.01); *G06T 19/20* (2013.01); *A61B 5/0013* (2013.01); *A61B 5/0071* (2013.01); *A61B 5/0075* (2013.01); *A61B 5/055* (2013.01); *A61B 8/0808* (2013.01); *A61B 19/5223* (2013.01); *A61B 2019/505* (2013.01); *A61B 2019/507* (2013.01); *A61B 2019/5255* (2013.01); *A61B 2019/5276* (2013.01); *A61B 2019/5295* (2013.01); *G06T 2200/08* (2013.01); *G06T 2207/10021* (2013.01); *G06T 2207/10028* (2013.01); *G06T 2207/30004* (2013.01); *G06T 2207/30096* (2013.01)

(56) References Cited

U.S. PATENT DOCUMENTS

| | | | |
|---|---|---|---|
| 6,208,886 B1 | 3/2001 | Alfano et al. | |
| 6,661,571 B1 | 12/2003 | Shioda et al. | |
| 6,793,350 B1 * | 9/2004 | Raskar | G03B 37/04 353/121 |
| 7,387,802 B2 | 6/2008 | Sambanthamurthi et al. | |
| 7,804,075 B2 | 9/2010 | Ntziachristos et al. | |
| 8,406,859 B2 | 3/2013 | Zuzak et al. | |
| 2004/0015062 A1 | 1/2004 | Ntziachristos et al. | |
| 2005/0085732 A1 | 4/2005 | Sevick-Muraca et al. | |
| 2006/0024390 A1 | 2/2006 | Schauss et al. | |
| 2007/0038126 A1 | 2/2007 | Pyle et al. | |
| 2007/0083124 A1 | 4/2007 | Ehben et al. | |
| 2007/0145136 A1 | 6/2007 | Wiklof et al. | |
| 2007/0236514 A1 * | 10/2007 | Agusanto | A61B 1/00193 345/646 |
| 2007/0238957 A1 | 10/2007 | Yared | |
| 2008/0218727 A1 | 9/2008 | Djeziri et al. | |
| 2008/0267472 A1 | 10/2008 | Demos | |
| 2009/0036902 A1 * | 2/2009 | DiMaio | A61B 8/12 606/130 |
| 2009/0295910 A1 | 12/2009 | Mir et al. | |
| 2011/0183370 A1 | 7/2011 | Noiseux et al. | |
| 2011/0222757 A1 | 9/2011 | Yeatman, Jr. et al. | |
| 2011/0275932 A1 | 11/2011 | Leblond et al. | |
| 2012/0133740 A1 | 5/2012 | Klimov et al. | |
| 2014/0063241 A1 | 3/2014 | Li et al. | |
| 2015/0264340 A1 * | 9/2015 | Seidl | G06T 15/10 348/36 |

FOREIGN PATENT DOCUMENTS

| | | |
|---|---|---|
| WO | 2007111570 A2 | 10/2007 |
| WO | 2009061425 A1 | 5/2009 |
| WO | 2013109966 A1 | 7/2013 |

OTHER PUBLICATIONS

PCT Application PCT/US2013/024400 International Search Report and Written Opinion dated May 15, 2013, 12 pages.
PCT Application PCT/US2014/016291 International Search Report and Written Opinoin dated May 27, 2014, 13 pages.
Fan, X., et al. "Simulation of Brain Tumor Resection in Image-Guided Neurosurgery," Medical Imaging 2011: Visulization Image-Guided Procedures, and Modeling, Proc. of SPEI Proceedings vol. 796, pp. 1-11, Mar. 2, 2011.
Sun, H., et al, "Stereopsis-Guided Brain Shift Compensation," IEEE Trans Med. Imaging, vol. 25, No. 8, pp. 1039-1052, Aug. 2005.
U.S. Appl. No. 13/145,505 select File History dated Mar. 27, 2013 through Sep. 30, 2014.
PCT Patent Application PCT/US14/51356 International Search Report and Written Opinion dated Dec. 9, 2014, 9 pages.
U.S. Appl. No. 14/370,712 Office Action dated Feb. 2, 2016, 25 pages.
Joshi, "DigiWarp: a method for deformable mouse atlas warping to surface topographic data", NIH Public Area, 2010, 25 pages.

* cited by examiner

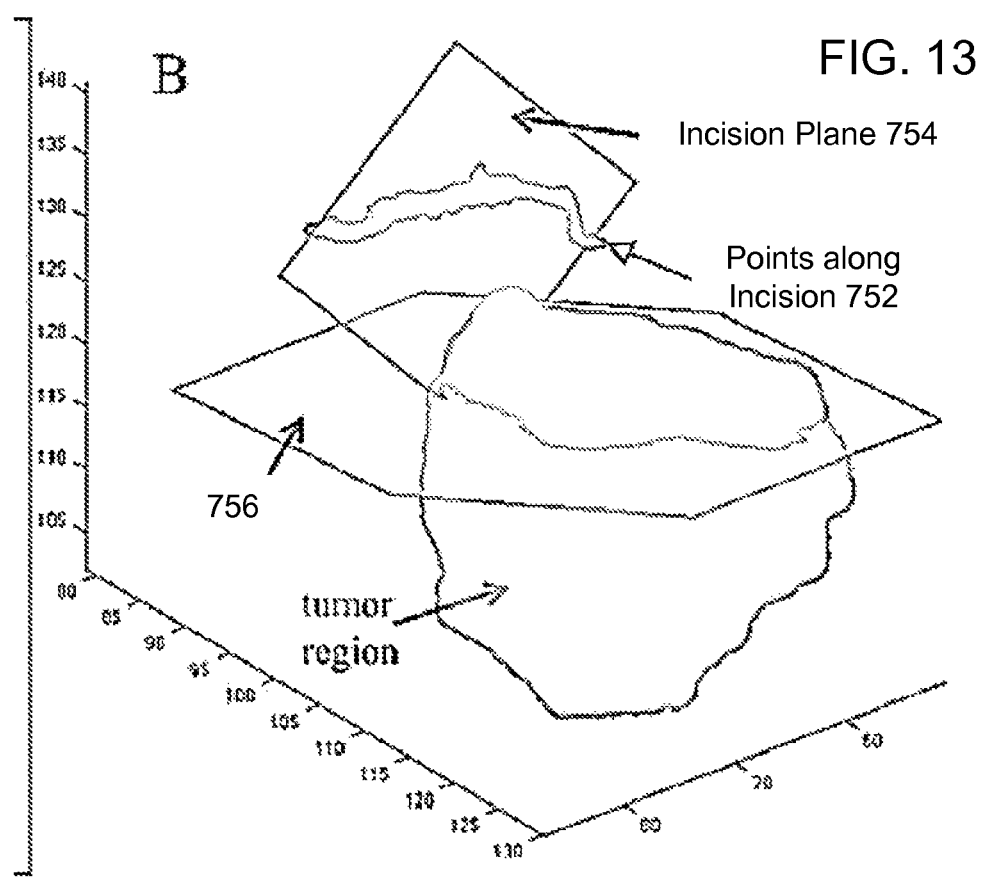

METHOD AND APPARATUS FOR DETERMINING TUMOR SHIFT DURING SURGERY USING A STEREO-OPTICAL THREE-DIMENSIONAL SURFACE-MAPPING SYSTEM

RELATED APPLICATIONS

The present application claims priority to U.S. Provisional patent application 61/594,862 filed Feb. 3, 2012. This application is a continuation-in-part of PCT Patent Application Serial No. PCT/US13/20352 filed 4 Jan. 2013, which claims priority to U.S. Patent Application Ser. No. 61/583,092, filed Jan. 4, 2012. The disclosures of the above-referenced applications are incorporated herein by reference.

This is related to U.S. patent application Ser. No. 13/145,505, filed in the United States Patent and Trademark Office on Jul. 20, 2011 which is a U.S. National Phase application of PCT Patent Application PCT/US09/66839 filed Dec. 4, 2009, which claims priority to U.S. Provisional Patent Application 61/145,900. This is also related to PCT Patent Application Serial No. PCT/US13/22266 filed Jan. 18, 2013, which claims priority to U.S. Provisional Application Ser. No. 61/588,708, filed Jan. 20, 2012. The disclosures of the above-referenced applications are incorporated herein by reference.

GOVERNMENT RIGHTS

This invention was made with government support under grant numbers R01 CA159324-01, R01 EB002082-11 and 1R21 NS078607 awarded by the National Institutes of Health. The government has certain rights in the invention.

FIELD

The present document pertains to the field of methods and apparatus for determining intraoperative locations of tumors or other inclusions and structures in mammalian tissues while performing surgery. In particular, this document relates to using a stereo 3-dimensional surface-mapping device to extract surface profiles and surface features of the tissue, automatically registering those surface features to features found in preoperative imagery, and using displacements of the surface features, determined surgical cavity volume and location, and presence and location of surgical tools to determine intraoperative displacements of the tumors or other inclusions and structures.

BACKGROUND

When performing surgical procedures on the brain, and some other soft organs, it is desirable to remove as much as possible of targeted tissue, such as a tumor or cyst, while preserving as much as possible of surrounding normal tissue. It is also necessary to avoid injury to specific critical structures to avoid inflicting unnecessary impairment on the patient. Typically, both targeted tissue and critical structures are mapped during preoperative magnetic resonance imaging (MRI) and/or computed tomography (CT) scans as part of pre-surgical diagnosis and planning.

When the skull is opened, the brain tends to deform because the brain is very soft, with the skull opened it is no longer confined and can sag under gravity, and because the brain is subjected to alterations in cerebro-spinal fluid (CSF) and blood pressure. The deformation may cause an apparent shift in location of structures mapped during preoperative imaging; this shift may exceed one centimeter. While these structures may be re-located with intra-operative MRI or CT scans, such scans are cumbersome and time consuming to perform and repeated scans may be required as tissue shifts with repositioning of retractors or as portions of tissue are removed. In particular, portions of the brain may sag or shift as other portions of tissue are resected, since resection may alter the fluid plane and the brain may start to sag along the gravitational direction. As a resection cavity goes deeper into the brain, the walls of the cavity may collapse due to gravitation and release of stress in the tissue. The brain deformation due to resection can significantly degrade the accuracy of image guidance. In order to perform the highest quality of neurosurgery within reasonable operative duration, a surgeon must precisely determine intraoperative positions of those targeted tissue and critical structures so that targeted tissue may be removed while preserving nearby or adjacent critical structures.

Similar distortions of tissue shape during surgery may also occur during surgical procedures on other organs as pressures on those organs change from those present during preoperative imaging to those present during surgery.

Electronic stereovision is used for mapping three-dimensional surface structures in a variety of applications. Previously, stereo-optical surface-mapping has been used to map a surface of the brain as deformed after the skull has been opened, a brain deformation model was then used to determine post-opening, and post-tissue-retraction, locations of targeted tissue and critical structures as these locations have shifted from those mapped during preoperative imaging. A PhD thesis describing how a surface map is used with a brain deformation model to determine a tumor shift may be found as Hai Sun, *Stereopsis-Guided Brain Shift Compensation, A Thesis*, Thayer School of Engineering, Dartmouth College, Hanover, N.H., May 2004, (Hai Sun) the contents of which are incorporated herein by reference.

Hai Sun uses correspondence point triangulation to determine a surface map, and discloses mechanical modeling of an organ, such as the brain, without compensation for additional factors such as surgical cavities in the organ or displacement of tissue by retractors or other surgical instruments. It has been found that the surface map extraction and tumor shift algorithms of Hai Sun fail under some conditions of surface texture. Further, it has been found that there can be significant differences between predicted and actual brain tumor locations if intraoperative surgical cavities and tissue displacement by instruments are not taken into account.

In *Simulation of Brain Tumor Resection in Image-guided Neurosurgery* Xiaoyao Fan, Songbai Ji, Kathryn Fontaine, Alex Hartov, David Roberts, Keith Paulsen Proc. SPIE 7964, Medical Imaging 2011 (Fan et al. 2011): Visualization, Image-Guided Procedures, and Modeling, 79640U (Mar. 1, 2011); many of the present applicants have discussed an earlier way of determining tumor shift taking into account both intraoperative ultrasound data and stereovision-derived surface map data. The method described in Fan et al, 2011, used a correspondence point method to extract surface maps, then ran a mechanical model with correspondence point displacements at the resection cavity to revise the cavity shape and size, and determine a new, post-resection, mesh model quantity of removed tissue, the new mesh model refined by an iterative process.

Another PhD thesis that discusses use of surface maps obtained with a stereo optical system during neurosurgery is *Later Stage Brain Deformation Compensation In Image-Guided Neurosurgery* by Xiaoyao Fan, Thayer School of Engineering, Dartmouth College, Hanover, N.H., May 2012, (Fan thesis) the contents of which are incorporated herein by reference. The Fan thesis discusses ways to account for intraoperative surgical cavities and tissue displacement by instruments, thereby providing more accurate predicted intraoperative brain tumor locations.

It is desirable to improve the accuracy and computing speed with which locations of targeted tissue and critical structures are tracked during this deformation, and to more rapidly compute their post-deformation locations.

SUMMARY

A method for determining an intraoperative location of a lesion in mammalian tissue of an organ from lesion locations determined in preoperative imaging includes determining three dimensional locations of surface features of the organ in the preoperative images. A preoperative surface map is extracted from stereo images annotated with the surface features from preoperative images. An intraoperative surface map of the organ is extracted from stereo images, and surface features are identified in the stereo images corresponding to surface features annotated into the preoperative surface map. Three dimensional displacements of the surface features are determined and used to constrain a computer model of deformation of the organ. The model of deformation is used to determine intraoperative locations for the lesion.

In an embodiment, method for determining a 3D model of a surface includes calibrating 3D reconstruction parameters for at least one reference setting of an optical system; calibrating image warping parameters for at least one secondary calibration setting, the image warping parameters adapted to control an image warping routine to warp images taken at that secondary calibration setting into warped images corresponding to images taken at the reference setting; taking an stereo image through the optical system with the optical system at a current setting; determining warping parameters from the image warping parameters for at least one secondary calibration setting of the at least one secondary calibration settings, the warping parameters for warping the stereo image taken at the current setting into a warped stereo image corresponding to a stereo image taken at the reference setting; warping the stereo image into the warped stereo image; determining three-dimensional (3D) warping parameters for warping a first image of the warped stereo image into a second image of the stereo image; and using the 3D warping parameters for determining the 3D model of the surface.

In another embodiment, a system for determining a 3D model of a surface includes an optical system having a plurality of settings, each setting providing a specific focal length and magnification, the optical system comprising an encoder for observing a current setting of the optical system; a memory configured to contain calibrated 3D reconstruction parameters for at least one reference setting of the optical system; the memory further configured with image warping parameters for at least one secondary calibration setting, the image warping parameters adapted to control an image warping routine to warp images taken at that secondary calibration setting into warped images corresponding to images taken at a reference setting of the at least one reference setting; a camera coupled to capture stereo images through the optical system; a processor configured with machine readable instructions in the memory, the machine readable instructions comprising instructions for determining warping parameters from the image warping parameters for at least one secondary calibration point, the warping parameters for warping the stereo image into a warped stereo image corresponding to a stereo image taken at the reference point; the memory further configured with machine readable instructions for warping the stereo image into the warped stereo image; the memory further configured with machine readable instructions for determining three-dimensional (3D) warping parameters for warping a first image of the warped stereo image into a second image of the stereo image; the memory further configured with machine readable instructions for using the 3D warping parameters for determining the 3D model of the surface.

In another embodiment, a method for determining intraoperative location of a lesion in mammalian tissue of an organ from preoperative imaging includes: determining a three dimensional location of the lesion in preoperative images; determining three dimensional locations of surface features of the organ in the preoperative images; determining a preoperative surface map of the organ; determining an intraoperative three dimensional surface map of the organ incorporating locations of the surface features; determining three dimensional displacements of the surface features between their positions in preoperative images and their positions in the intraoperative three dimensional surface map of the organ; constraining a computer based model of deformation of the organ with both the intraoperative three dimensional surface map and the three dimensional displacements of the surface features; and applying the computer based model of deformation to determine intraoperative locations of the lesion.

BRIEF DESCRIPTION OF THE FIGURES

FIG. 13 is an illustration of finding an incision plane and incision depth or focal plane.

DETAILED DESCRIPTION OF THE EMBODIMENTS

Some concepts herein described have been published as Fan, X., Ji, S., Hartov, A., Roberts, D., Paulsen, K., "Registering stereovision surface with preoperative magnetic resonance images for brain shift compensation" in Medical Imaging 2012: Image-Guided Procedures, Robotic Interventions, and Modeling, edited by David R. Holmes III, Kenneth H. Wong, Proceedings of SPIE Vol. 8316 (SPIE, Bellingham, Wash. 2012) 83161C, the contents of which are incorporated herein by reference.

Figure 1:
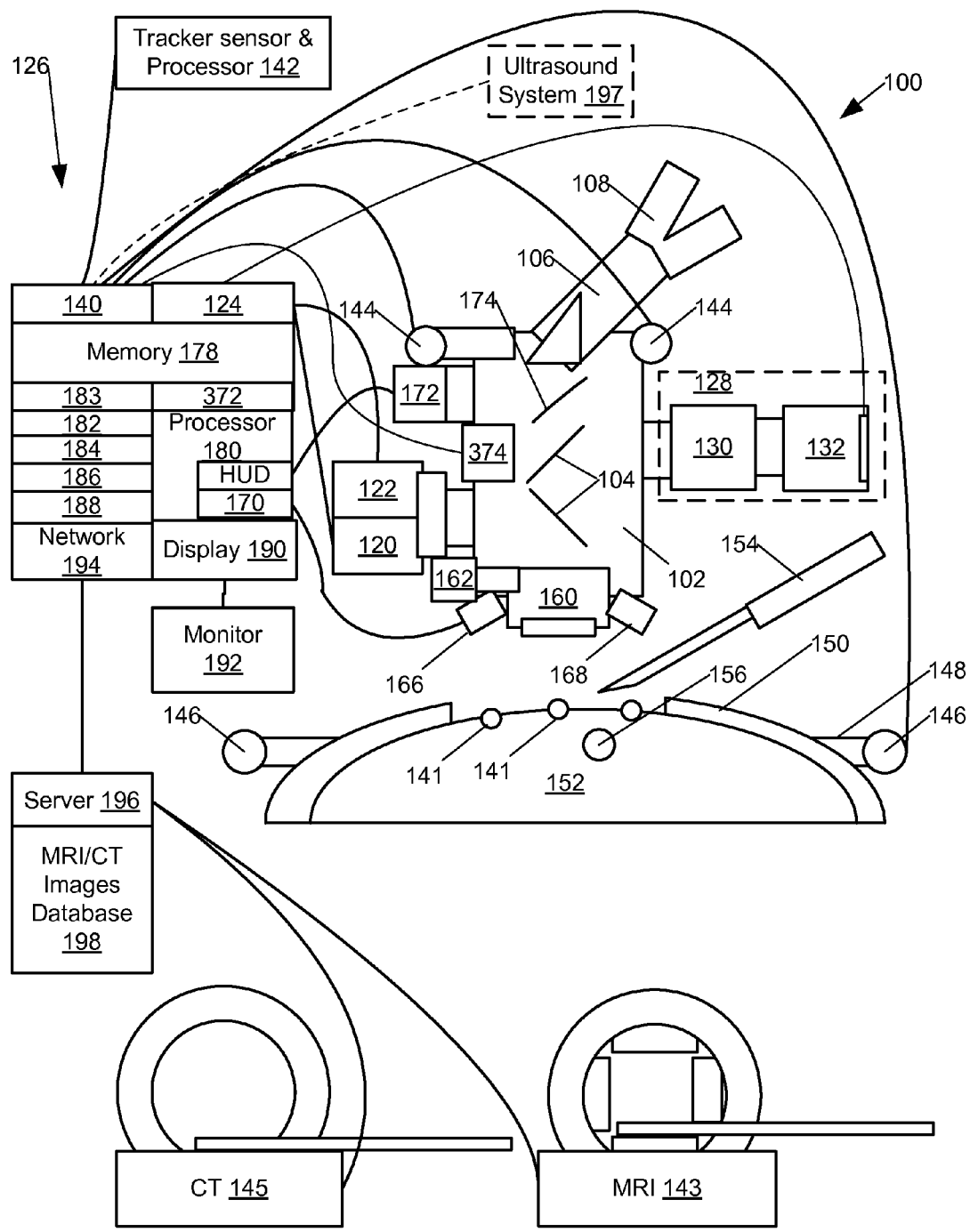
FIG. 1 is a diagram of one exemplary system for assisting a surgeon in locating structures in soft tissues during surgery, in an embodiment.

FIG. 1 illustrates a system 100 for supporting surgery, according to some embodiments. The system of FIG. 1 includes a microscope body 102, which has multiple beam splitters 104 that permit light to be diverted to several optical ports simultaneously. Attached to a first optical port of body 102 is a tube 106 leading to a surgeon's binocular optical eyepieces 108.

Attached to a second optical port of body 102 are a first high definition electronic camera 120 and a second high definition electronic camera 122. Cameras 120, 122 are coupled to provide images to image capture interface 124 of a digital image processing system 126. Attached to a third optical port of body 102 is a hyperspectral imaging device 128 that in an embodiment has a tunable filter 130 adapted to receive light from body 102 and a high resolution broad-bandwidth electronic camera 132. The camera 132 of the hyperspectral imaging device 128 is also coupled to provide images to image capture interface 124 of the digital processing system 126. In an embodiment, tunable filter 130 is a liquid crystal tunable filter. In an alternative embodiment, tunable filter 130 is an acousto-optic tunable filter.

Referring again to FIG. 1, a tracker interface 140 of the image processing system 126 is coupled to use tracking sensors 142 attached to a reference location within an operating room to track relative locations of microscope location sensors 144 and patient location sensors 146. In an embodiment, tracking sensors 142 and an associated processor of tracker interface 140 are a commercially available Treon® StealthStation®, (trademarks of Medtronic, Louisville, Colo., USA) optical tracking system. Microscope location sensors 144 are rigidly attached to the microscope body 102, and patient location sensors 146 are attached to a frame 148 that may be attached to a patient while the patient is undergoing a surgical procedure. In a particular embodiment, frame 148 is adapted to be attached to a patient's skull 150 by screws (not shown) for the duration of a neurosurgical procedure during which the patient's brain 152 is exposed, and during which patient's brain 152 may be operated on with surgical instruments 154 to remove one or more lesions 156.

Microscope body 102 also has zoom optics 160, adapted for operation by a zoom motor/sensor 162, and a focus adjustment (not shown) adapted for operation by a focus motor (not shown). The microscope also has multiple illuminators 166, 168. In an embodiment, illuminators 166 include white-light illuminators 166, and fluorescent stimulus illuminators 168, operating under control of an illumination interface 170 of the image processing system 126. The microscope body also has a heads-up display (HUD) projector 172 capable of providing graphical images through a combiner 174 of body 102 such that the graphical images are presented for viewing by a surgeon through surgeon's eyepieces 108. The surgeon's field of view through the operating microscope and its associated HUD is co-registered with that of the imaging system, allowing display of tissue classifications, mapped tumor locations, and hyperspectral imaging results superimposed on visible brain tissue, one-to-one comparisons, and intraoperative surgical decision making. At standard working distances between microscope and surgical cavity, surgical instruments 154 fit between zoom optics 160 and tissue of brain 152.

Image processing system 126 also has a memory 178 into which image capture interface 124 saves images received from cameras 120, 122, 132; and at least one processor 180. Processor 180 is adapted for executing processing routines such as surface profile extraction routines 182, image deformation or warping routines 183, brain deformation modeling routines 184, fluorescence depth modeling routines 186, and hyperspectral image processing routines 188 stored in memory 178 and operable on images stored in memory 178. Processor 180 is also adapted for preparing images for display through display interface 190 onto monitor 192, and for communicating through network interface 194 to server 196; server 196 has a database 198 containing information derived from preoperative MRI and CAT scans.

Among the image processing routines in memory of image processing system 126 is a classifier for classifying tissue types according to a combination of fluorescence and backscatter information. In a particular embodiment, the classifier is a K-nearest-neighbor classifier.

Server 196 is also interfaced through a network to an MRI scanner 143 as known in the medical imaging art that provides high resolution preoperative images of a patient's brain 152, including surface features 141, and tumor 156, prior to prepping the patient for surgery and opening the patient's skull 150 (brain 152, tumor 156, surface features 141 are shown with patient prepared for surgery and skull opened). Server 196 is also interfaced through a network to a CT scanner 145 that is capable of imaging a patient's brain prior to prepping the patient for surgery and opening the patient's skull 150.

Operation of the system 100 has several modes, and each mode may require execution of several phases of processing on processor 180, executing one or more of several routines, as mentioned above. Computational efficiency and high performance are desirable in processor 180, since it is desirable to minimize the operative time for which a subject is anesthetized.

For example, processor 180 executes the hyperspectral image processing routine to perform the hyperspectral fluorescence and reflectance imaging of the system, as described above in detail. The hyperspectral fluorescence and reflectance imaging may also be performed in connection with stereo-optical extraction, using images captured by stereo cameras 120, 122, to perform tissue surface contour and feature extraction. The hyperspectral fluorescence and reflectance imaging may also be performed in connection with fluorescence depth modeling, as described in U.S. patent application Ser. No. 13/145,505, filed in the United States Patent and Trademark Office on Jul. 2, 2011, and U.S. Provisional Patent Application 61/588,708, filed on Jan. 20, 2012 and incorporated herein in its entirety by reference, and described below in detail, where fluorescence and reflectance spectral information is derived from hyperspectral imaging device 128.

In some embodiments, an optional ultrasound system 197 is provided to map deep brain structures using medical ultrasound as known in the art. In some embodiments, information from the ultrasound system 197 is coregistered with information from the stereo optical system herein described and jointly used for modeling shift of deep brain tumors and structures, particularly where surgical cavities exist and/or surgical instruments, such as retractors, are present in a surgical site.

Figure 1A:
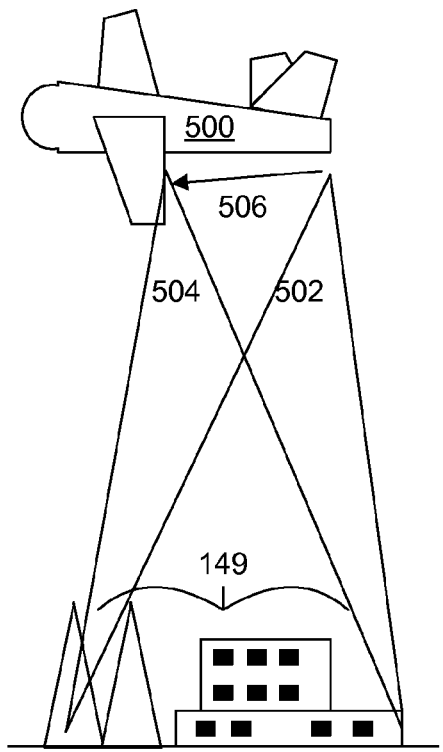
FIG. 1A is a diagram of an alternative embodiment of an optical system for capturing stereo pairs of images that may be processed by the image processor.

Many of the features and methods herein described are applicable to other optical systems, such as the aerial reconnaissance system of FIG. 1A, where a stereo image is a sequence of images taken by a camera in an aircraft or drone 500; in such an embodiment a first or "left" image taken from a first angle 502 or position and a second image taken from a second angle 504 or position are processed as a stereo pair with a known distance 506 between the positions from which images of the pair are taken.

System Functions

Figure 2:
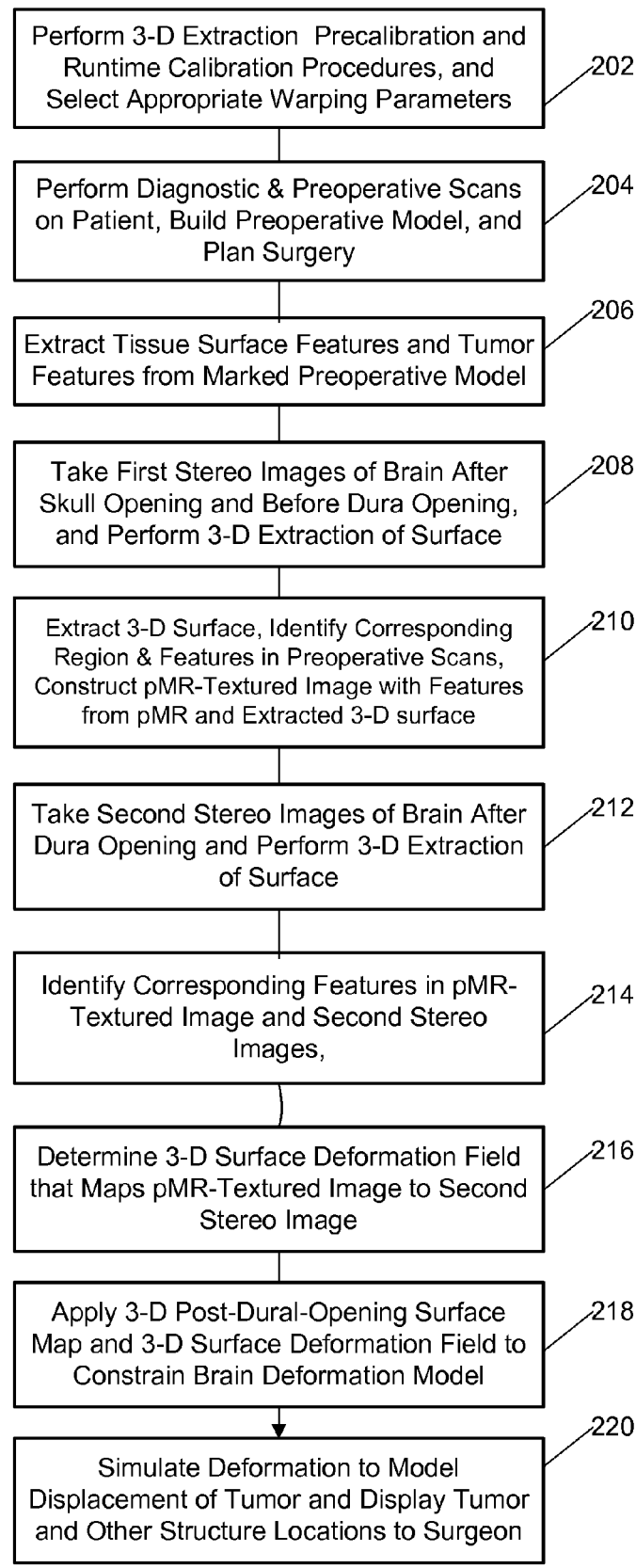
FIG. 2 is a flowchart of one exemplary method for determining post-deformation locations of structures in soft tissues during surgery, in an embodiment.
Figure 3:
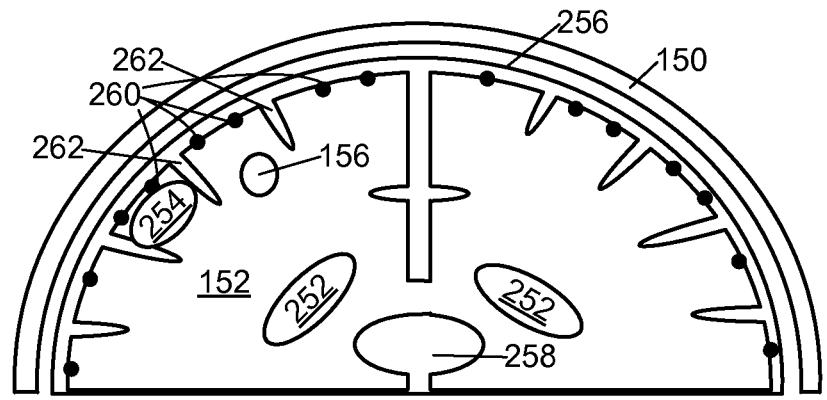
FIG. 3 shows a cross-sectional illustration of a brain, such as a human brain, with skull and meninges.

Patients are prepared, the system is operated, and surgery performed, according to the flowchart of FIG. 2. The system of FIG. 1 is prepared and calibrated 202 for proper three-dimensional surface extraction, according to the procedure outlined below. FIG. 3 shows a cross-sectional illustration of the brain 152 of FIG. 1, showing skull 150 and meninges. FIGS. 1, 2, and 3, are best viewed together with the following description.

The patient is subjected to appropriate diagnostic and pre-operative MRI (Magnetic resonance Imaging) and/or CT (Computed Tomography X-ray) scans. These preoperative (pMR) scans provide a preoperative three-dimensional model of tissue of the patient, in a particular embodiment the tissue of the patient includes the patients' brain 152 (FIG. 1 and FIG. 3). A surgeon performs preoperative planning 204, which includes identifying lesion tissue, such as tumor tissue 156, as targeted tissue for removal in the preoperative model of the tissue. The preoperative planning may also include identifying other important structures 252, such as particular blood vessels, nerve tracts, nearby areas critical for particular functions such as Broca's area 254, and other nearby structures that the surgeon desires to preserve during operation. The tumor tissue 156 targeted for removal, and other important structures 252, 254 that are desired to be preserved, are marked in the preoperative model at their locations as provided in the preoperative scans, indicating their respective locations before surgery begins. The preoperative model established from preoperative scans are detailed and visualize some brain surface structures, such as blood vessels 260, and sulci 262; sulci (plural of sulcus) are creases or folds at the surface of the brain. The surface of the dura is presumed to be at the surface of the brain as shown in the pMR model and scans. A model of the surface of the brain is extracted from the pMR model and scans. The pMR model is in a patient-centered coordinate system.

Once consent is obtained, the patient is prepared for surgery, and patient tracking sensors 146 are attached to the patient's skull. The patient tracking sensors are registered to the patient-centered coordinate system of the pMR model. Positions of the patient tracking sensors are determined in the patient-centered coordinate system, and the patient's skull 150 is opened, exposing the dura 256 matter. The dura matter is the tough and fibrous part of the meninges, the meninges are membranous coverings of the brain located between skull 150 and brain 152, and contain the brain as well as cerebrospinal fluid (CSF) that bathes the brain and fills openings within the brain such as ventricles 258.

Figure 4:
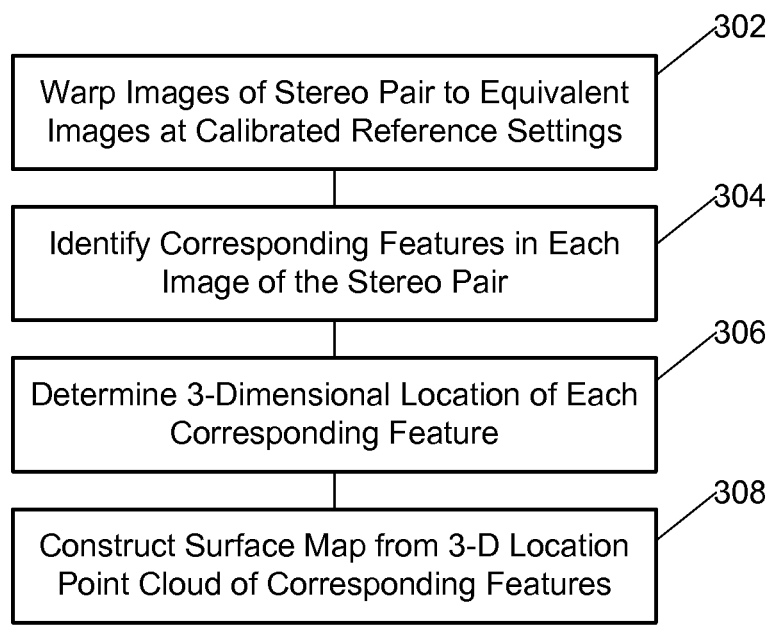
FIG. 4 is an exemplary flowchart of a method for determining a three dimensional surface map, in an embodiment.

Surgery begins. Once the skin and skull are opened and before opening the dura, the microscope zoom optics 160 and focus are set to a desired runtime optical setting, and the microscope body 102 position is adjusted such that it is over the surgical wound and a field of view of the microscope includes dura over brain tissue 152 over the tumor 156. The microscope location and orientation is tracked relative to the patient using tracking sensors 142, microscope location sensors 144 and patient tracking sensors 146. A first pair of stereo images is then taken 208. Once taken, this first pair of stereo images is then processed using any features visible on the dural surface as follows:

a) Stereo visual surface extraction (FIG. 4) is performed of the dural surface in the images to create a dural surface map by 1) Warping 302 the images to equivalent images as if taken at the reference settings;
2) Identifying 304 corresponding features in both warped images;
3) Tracing rays from the corresponding features to determine 306 three-dimensional locations of those features, the 3-dimensional locations forming a point cloud;
4) Constructing 308 an extracted dural surface map from the point cloud of three-dimensional locations.
5) Transforming the extracted dural surface map to the patient-centered coordinate system of the pMR model by applying any necessary rotations and translations.

b) Correlating the pre-opening surface map with dural surface as observed in the pMR model and scans.

c) A pMR-textured surface map is constructed 210 from the extracted dural surface map, annotated with positions of brain surface features, such as blood vessels and sulci that are visible in the pMR model and images.

In an alternative embodiment, an alternative pMR surface map used in place of the pMR texture map/pre-durotomy surface is generated using the post-durotomy surface using a method including:

1. The brain is segmented from the full-head pMR images, leaving a pMR model or image stack that only contains the un-deformed brain and excludes other parts of the head such as scalp, skull, etc.
2. A triangular surface mesh (pMR mesh) is generated of brain surface of the pMR model or image stack.
3. An intraoperative stereo image pair is acquired after dural-opening; the corresponding surface is reconstructed and registered with the pMR images or model.
4. A surface (triangular) mesh is generated using the reconstructed stereovision point cloud to give a post-durotomy mesh. And a surface normal can be extracted, by averaging the surface normals of all triangles.
5. The post-durotomy mesh is projected along the surface normal, onto the brain surface mesh, to form a second mesh on the un-deformed brain surface of the pMR mesh, and aligned with the brain surface in pMR.
6. The second mesh is annotated with features, such as blood vessels and sulci, extracted from the pMR model to form a pMR-based texture map.

This alternative method does not require capture of an intraoperative stereo image pair before dural-opening. We have tried this method on 12 patient cases and it works. This alternative method is especially useful if the surgeon has already cut open the dura and forgot to acquire images before dural-opening, and is immune to errors due to deformation that may occur after skull opening but before dural opening.

While some minor deformation occurs after skull opening but before dural opening, it has been found that the majority of deformation occurs after dural opening; the surface profile of the dura before opening the dura therefore closely resembles the dural surface as viewed in the pMR model. Similarly, blood vessels, sulci, and other surface features of the brain found in the pMR model remain close to their original locations until the dura is opened.

The dura is then opened, at which time some CSF spills and the fibrous and hydrodynamic support provided by the dura and CSF for the brain is lost; pressure of fluid in ventricles 258 and blood pressure also cause some swelling of the brain. The brain thereupon deforms into an intra-operative shape, swelling somewhat into the surgical wound as well as sagging with gravity, thereby displacing the brain surface, surface structures, including blood vessels 260 and sulci 262, as well as displacing both the tumor 156 and important structures 254, 252.

A second pair of stereo images is captured after opening the dura. A third, optional, pair of stereo images may be captured at later times during the surgery, as brain position is further disturbed with retractors and/or incisions.

After obtaining the second pair of stereo images, a post-dural-opening surface map is extracted by repeating steps 302-308 as follows:
1) Warping 302 the images to equivalent images as if taken at the reference settings;
2) Identifying 304 corresponding features in both warped images;
3) Tracing rays from the corresponding features to determine 306 3-dimensional locations of those features, the 3-dimensional locations forming a point cloud;
4) Constructing 308 an extracted post-dural-opening brain surface map from the point cloud of 3-dimensional locations.
5) Transforming or mapping the extracted post-dural-opening brain surface map into the patient-centered coordinate system.

Both pre- and post-dural-opening brain surface maps are then transformed and sized to a common grid to produce images having the same region of interest and pixel resolution. In an embodiment, this is done by:
1) In a local coordinate system, a triangular surface mesh is generated using pre-durotomy intraoperative stereovision point cloud in the image space (represented by x, y, and z axis), and the surface normal w is calculated by averaging the normal vectors of all elements. A second vector u is calculated by finding the cross product of the surface normal w and vector [1, 0, 0]. A third vector v is calculated by finding the cross product of vector u and v. Axes u, v, and w were perpendicular to each other and represent a local coordinate system, where w axis is parallel with the surface normal.
2) Five distinct points were defined in image space: [1, 0, 0], [0, 1, 0], [0, 0, 1], [1, 1, 1], and [1, 1, 0], and their corresponding coordinates in the local u-v-w coordinate system were: [u], [v], [w], [u+v+w], and [u+v]. A rigid transformation T is then found to match these two sets of points using an SVD (Singular Value Decomposition) algorithm.
3) Pre- and post-durotomy intraoperative stereovision point clouds are then transformed into the local u-v-w coordinate system following transformation T.
4) A two-dimensional grid parallel to the u-v plane is defined in the local coordinate system to form a set of sample points.
5) At the sample points, x, y, z coordinates and image intensities were computed using a scattered data interpolation method.

Next, corresponding surface features, such as blood vessels and sulci, visible in the post-dural-opening surface map and post-dural-opening stereo images, and also visible in the pMR textured surface map are identified 214. In an embodiment, this is performed by smoothing the images to retain larger shapes, then using a rigid mutual—information-based automatic image registration to detect global shift and gain error.

Figure 5A:
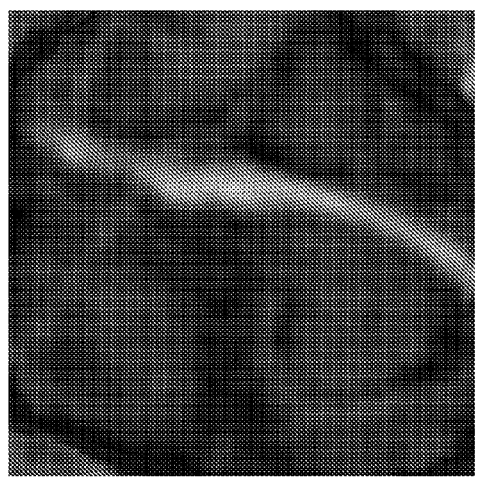
FIG. 5A shows pre-durotomy surface map annotated with features from the pMR model.
Figure 5B:
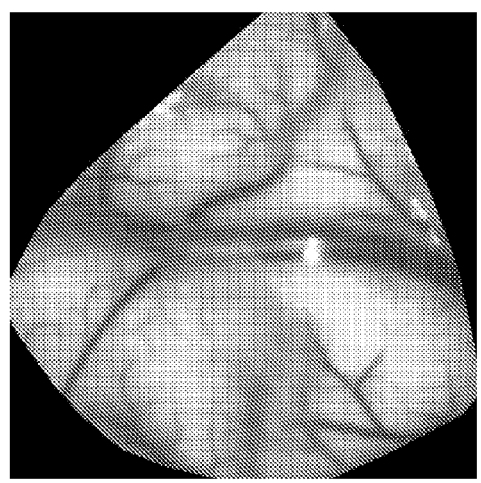
FIG. 5B shows a post-durotomy surface map.

In an alternative embodiment, detection of corresponding surface features is performed with an image thresh-holding method (Otsu's Method) applied to the images (pre-opening with features from the pMR model in FIG. 5A and post-opening surface map in FIG. 5B) to produce two black-and-white images that only contain dominant features such as large vessels and sulci. As can be seen from FIGS. 5A and 5B, vessels appear to be bright in image A (MR image) but dark in image B (photographic), so one of these two images needs to be inverted (so that dark becomes bright). Then a mean-square based image registration is applied to detect the global shift.

In an embodiment, the stereo image pairs are greyscale image pairs having slightly different points of view or viewing angles. In an alternative embodiment, the stereo image pairs are color image pairs also having slightly differing points of view.

While these features have similar shape and similar relative positions in both the pMR textured surface map and in the post-dural-opening surface map, their exact positions will differ because of post-dural-opening swelling and/or sagging of the brain. The detected global shift is applied to account for lateral movement of the brain, then a 2D nonrigid deformation field, representing local movement of the brain, is determined by using a block matching registration algorithm based on mutual-information to determine local shifts of each block. Although displacements within each block are rigid, displacements between blocks are not necessarily rigid, which provide nonrigid deformation globally. A 2D deformation field that maps the pMR textured surface map into the post-dural-opening surface map is then determined 216 by the processor from the global shifts and local shifts of the identified corresponding surface features. Since three-dimensional locations of each feature are known both in the pMR textured surface map and in the post-dural-opening surface map, a three dimensional deformation field of the brain surface can be determined by finding the 3D locations of the starting and ending points of each vector in the 2D displacement field.

A computer-simulated mechanical model of the brain is then constrained with remaining non-deformable skull external to a craniotomy boundary extracted from the pre-dural-opening stereo image pair. In an alternative embodiment, the craniotomy boundary is extracted from the post-dural-opening stereo image pair. The mechanical model is further constrained to distort the brain surface according to the 3-D Surface Deformation Model with resulting brain shape equal to the 3-D Post-Dural-Opening Surface Map. The mechanical model of the brain is then executed to simulate 220 displacements of the tumor 156 and other structures 252, 254.

Post-deformation simulated positions of tumor 156 and other structures 252, 254 are then displayed to the surgeon by processor 180 using the HUD, display interface 190, and monitor 192.

In an embodiment, the preoperative MRI (pMR) tomographic image stack is warped according to the deformation determined by executing the computerized mechanical model of the brain to form an updated MRI (uMR) image stack that depicts post-deformation locations of tumor and other structures in the brain.

Resection and Surgical Tool Modeling

Modeling of deformation using a 3D surface map obtained as herein described has been found to give locations of tumors and other specific structures in the brain, but these positions become increasingly inaccurate once surgical resection of tissue begins and a surgical cavity is formed in the organ or brain, or when tissue of the organ or tissue is displaced by surgical tools such as retractors. These inaccuracies result from loss of strength of tissue when cut, from changes in hydraulic pressure in the tissue due to alterations in cerebrospinal fluid and blood in the tissue, from resection forming a cavity into which portions of the tissue may sag, and other factors. Further, surgical tools, such as retractors, that may be present in tissue when intraoperative images are taken may cause additional errors.

In an embodiment, processor 180 is configured with optional resection volume estimation and effect modeling routines in memory 178 (resection modeling), the resection modeling routines containing machine readable instructions for determining a volume and location of tissue removed 482 and for adapting the mechanical model of tissue used for modeling tissue deformation to model detected incisions and surgical cavities, such that modeled tumor and critical structure locations are accurate even after surgery begins.

In an embodiment, processor 180 is configured with surgical tool detection and effect modeling routines in memory 178, the surgical tool modeling routines comprising machine readable instructions adapted to determine locations of surgical tools and for adapting the mechanical model of tissue to the presence and effect of those surgical tools on modeled locations of tumor and other structures. In an alternative embodiment, memory 178 contains both surgical tool detection and effect-modeling routines and surgical cavity extraction and modeling routines.

An issue in resection modeling is that no definitive knowledge of the shape and amount of resected tissue is available with prior surgical techniques. To solve this problem, and thereby obtain information required to update the computerized mechanical model of the brain such that accurate modeling of deformation is possible, a reasonable estimation is made using a 3D surface acquired after a current resection at a current surgical stage. This estimate is used to adapt the computerized mechanical model of tissue to compute displacements at the current resection cavity, based on which the estimation of tissue removal is revised, and the computerized mechanical model is re-run using the revised estimation of tissue removal to predict displacement of tumor and critical structures. These computed displacements are applied to tumor and critical structure locations from either intraoperative imaging or pre-surgical imaging to provide revised tumor and structure locations, and these locations are displayed to the surgeon to assist in any additional resections; in a particular embodiment the displacements are used to warp pMR images to provide uMR images, and the uMR images are displayed to operating room staff and the surgeon.

In a particular embodiment, the process of performing 3-D surface mapping, estimating resected tissue location and volume from the 3-D surface map, applying those estimates to the mechanical model of tissue, re-running the mechanical model as constrained by the 3-D surface map and adapted for resected tissue locations and volumes, to determine displacements of tumor and critical structures, and displaying determined tumor and critical structure locations to the surgeon are repeated multiple times during surgery.

Surface Mesh Based on Resection Cavity

The volume and location of tissue removal during an initial resection or sequence of resections is estimated using the stereovision-captured surface acquired at a current surgical stage.

In estimating volume and locations of tissue resected during a current surgical stage, the image stack from a "last known-correct" surgical stage, such as intraoperative MRI or CT tomographic images acquired prior to the current resection or surgical stage, or images from pre-surgical imaging pMR, is used to produce an initial surface mesh (ISM) model of the brain surface of shape of the brain before the current resection. In an alternative embodiment, an uMR image stack representing tumor and structure locations after prior stages of surgery is used to provide an ISM of brain surface, tumor locations, and critical structure locations before the current surgical stage.

A reconstructed 3D stereovision surface model is acquired after the current resection to determine a post initial resection model (PIR) that is overlaid onto the brain surface mesh. A region or regions corresponding to surgical cavity is selected from the PIR surface and the corresponding 3D coordinates of selected pixels are extracted from the PIR surface and overlaid onto the brain mesh. A dedicated meshing tool is used to subtract the PIR surface from the ISM to form a new closed 3D surface 482. If there are multiple resection sites in the current resection, the process is repeated on each resection site to give an initial estimate of the amount of tissue resection. This provides an outer surface model of the brain, a location for each resection, and an approximate volume for each resection.

Next, surface displacements on the surface between the current PIR and previous surgical stage ISM are extracted by generating an image warping field that provides a best match between surface structures that exist in images derived by projecting the PIR and ISM and corresponding image intensities onto a plane as an ISM-projection from before the current resections and a PIR-projection from after the current surgical stage or resections.

Due to different microscope positions and different microscope settings, the same craniotomy can appear differently in two stereo images. A stereo image pair from the PIR state is warped to a reference setting as previously described, which may be in a different coordinate system than the initial stereo image pair, and a current stereo image pair is warped to the same reference setting. An optical flow (OF) algorithm is used to determine an operative image warping field that maps the PIR image to the current images, with areas determined to be surgical cavity excluded from matching by applying a mask, so that only the displacements of unresected brain surface are extracted. In some cases, such as due to a change in lighting, the images may appear differently in terms of color and the registration based on color images may not be accurate. In this scenario, RGB color images are converted to grayscale images for determination of this operative warping field.

Figure 12:
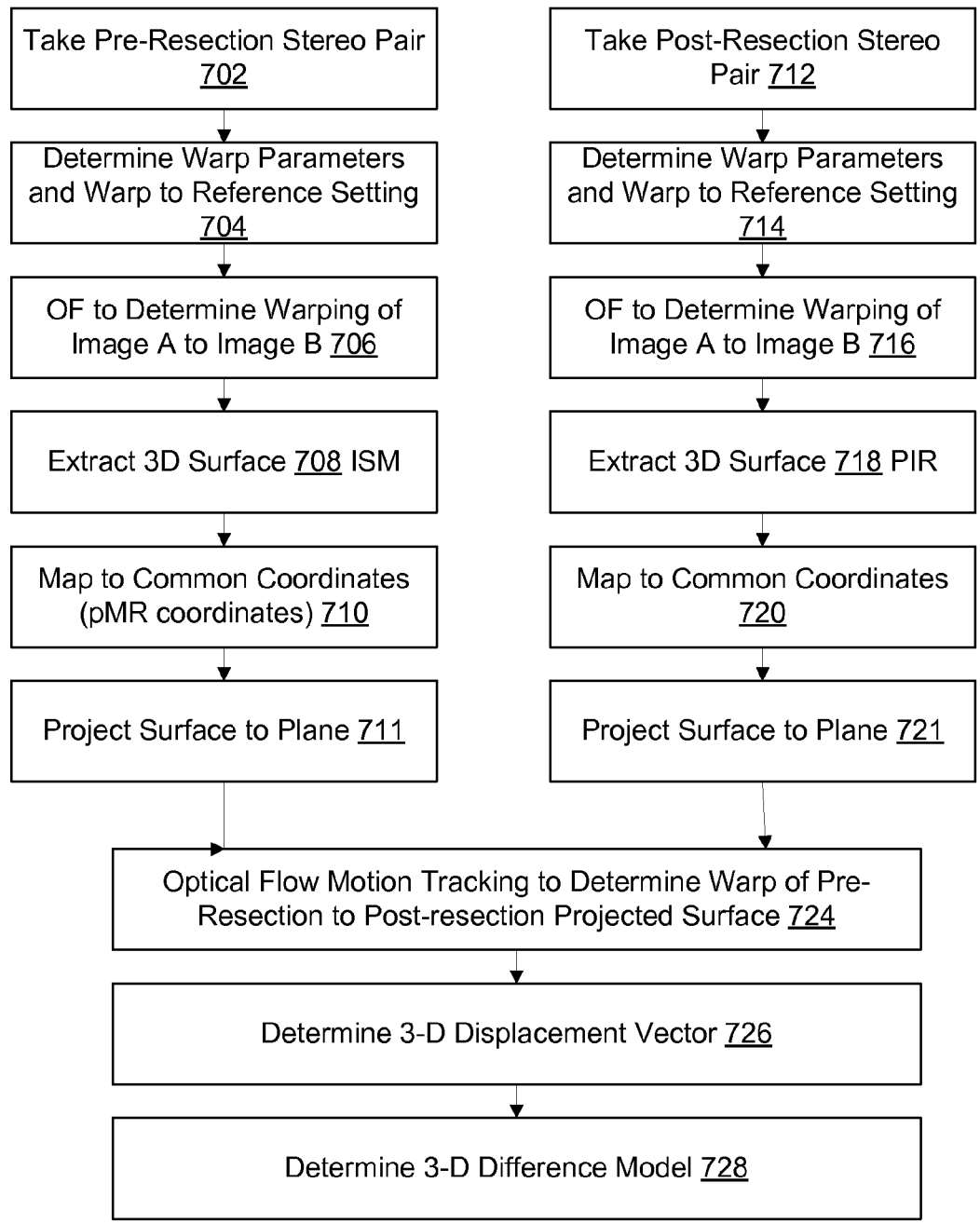
FIG. 12 is a flowchart illustrating estimation of volume of resection using an optical-flow method.

In an embodiment, as summarized in FIG. 12, a pre-resection (ISM images) stereo image pair is captured 702. Optical system settings are read from the encoders on the optical system, and these settings are interpolated into a table as previously described to determine image-warping parameters for warping the pre-resection stereo image pair to a calibrated reference setting, and the images are warped 704. An optical-flow method is used to determine 706 a warping of a first image of the pair to match a second image of the pair, the warping is used to derive 708 a 3-dimensional initial surface model ISM. The ISM is a 3-D model of an image, with intensities at each pixel derived from the ISM images. The ISM is coordinate remapped 710 to a common coordinate system, such as the coordinate system of presurgical MRI images (pMR). A post-resection (PIR images) stereo image pair is captured 712. Optical system settings are read from the encoders on the optical system, and these settings are interpolated into a table as previously described to determine image-warping parameters for warping the pre-resection stereo image pair to a calibrated reference setting, and the images are warped 714. An optical-flow method is used to determine 716 a warping of a first image of the pair to match a second image of the pair, the warping is used to derive 718 a 3-dimensional post-resection model PIR. The PIR is a 3-D model of an image, with a height at each pixel and intensities at each pixel derived from the PIR images. The PIR is coordinate remapped 720 to the common coordinate system. Both the ISM model and the PIR model are projected 711, 721 onto a common plane as ISM and PIR projections, respectively. An optical-flow process is then used to determine 724 a 2-dimensional image warping that will map the ISM to the PIR projection; in an alternative embodiment a 2-dimensional warping that maps the PIR projection to the ISM projection is determined. The spatial mapping of the ISM to the plane, and the PIR model to the plane is then inverted and subtracted to determine 726 a three-dimensional displacement vector of difference between the ISM and PIR models. The 3-D displacement vector in turn is used to derive 728 a 3D difference model (delta-M), a volume of the difference model being an initial estimate of the volume of resected tissue. In an alternative embodiment, the spatial mappings of the ISM to the plane and PIR to the plane are determined at planar grid points, inverted, and subtracted to determine 728 the three-dimensional difference model.

The amount of brain tissue removed from the mesh is not necessarily the true amount of, or shape of, tissue removal relative to the PIR model because of brain sagging and lateral shift. To compensate for brain deformation between two surgical stages, an iteration using an inverse model is applied to refine the resection volume and dimensions, the inverse model, driven by extracted sparse data from stereovision to prepare an improved estimate of brain deformation after tissue resection. The resulting amount of brain shift (including sagging and lateral shift) at the resection sites indicates the error in previous estimation of the amount of tissue removal. To correct the error in previous estimation, first, for each resection cavity, the outer boundary of the stereovision surface (isolated surface corresponding to the resection area only) is extracted, fitted to a plane, and projected onto a plane to form a polygon. The brain surface mesh is then projected into the polygon along the average stereovision surface. Points that fall inside the polygon are considered inside the resection cavity, and the displacements at these points are used to revise the amount and/or shape of tissue removal. Then, a new tetrahedral mesh is generated using the new brain surface where brain volume inside the revised resection cavities has been removed. A new set of boundary conditions is generated accordingly. The buoyancy driving force is determined from the new fluid level plane perpendicular to the gravity vector, then the deformation model is applied to estimate brain deformation and produce updated MR.

Updating Pre-Surgical Images to Show Resection

It may be desirable to illustrate surgical progress such that a surgeon may determine what has been accomplished during surgery, and gauge progress according to a surgical plan. In an embodiment this is done by updating or annotating pre-surgical imaging. In a particular embodiment, this is done by blanking out pixels corresponding to resected tissue in pre-operative images, or, in an alternative embodiment, marking pixels corresponding to resected tissue with a particular color to indicate that those portions have been removed.

An updated brain mesh is generated using the same approach as described above, where the PIR surface corresponding to the resection cavity is used to determine the outer surface of the brain, and the same procedure is repeated for each resection cavity.

To provide the MR stack to be deformed using model computation results, the voxels inside the resection cavities are removed from the "last-known-correct" MR, similarly to an approach to remove points inside resection cavity from the MR stack. Specifically, a bounding box in the MR stack is defined using the PIR stereovision surface, and MR voxels inside the bounding box are compared with the outer surface of the brain mesh (a closed surface), and those voxels that are outside the closed surface are considered been resected, and removed from the MR stack. A set of new boundary conditions is assigned using the new brain mesh. The deformation model is driven by surface displacements extracted using the OF algorithm Combined Intraoperative Stereovision and Ultrasound.

When intraoperative ultrasound (iUS) is available, such as provided by an ultrasound system 197, both intraoperative stereovision (iSV) data and iUS data from ultrasound system 197 representing structures of both surface and deeper brain is used for the update computation. Sparse data extracted from iUS is used together with those from iSV surfaces to drive the computational model. In an embodiment iUS data are used to detect brain deformation and validate uMR in deeper brain, while iSV is used to determine the amount of tissue removal and surface movement, and validate uMR at the untouched cortical surface as well as the resection cavity. There have been surgery cases where iUS showed the boundary of the cavity clearly. Hence, if and when iUS shows the boundary of the surgical cavity, iUS may also be able to detect the amount of tissue removal, and cross-validate the iSV surface.

Intraoperative US is especially helpful when part of a surgical cavity is beneath untouched cortical surface. For example, if the tumor is deep in the brain and retractors are used to split the tissue above the tumor region, then at the end of resection when the retractors are removed from the surgical field and brain tissue is relaxed, the cortical surface may cover part of the resection cavity, and the correct shape of cavity cannot be recovered from iSV data, as the cameras cannot capture subsurface data. In this case, ultrasound may be used to provide a better estimation of the shape of cavity.

Revision of the iSV surface based on model estimates in the approach described above is required in order to estimate the correct amount of tissue removal. This is in part because if the raw iSV surfaces are used to carve out the voxels in the MR image stack to produce uMR, accuracy is degraded by the amount of brain shift at those resection cavities. Therefore, we apply an inverse scheme and revise the iSV surface accordingly to determine the correct amount of tissue removal.

Surgical Instrument and Retraction Modeling

When a tumor is superficial, the surgeon starts resecting it as soon as the dura is open. In cases where the tumor is deeper in the brain, the surgeon may first dissect from the cortical surface into the brain tissue along the surgical trajectory to reach the tumor. In this process, surgeon may use retractors or other surgical tools to separate the edges of the incision, and it may take up to an hour to finally reach the tumor. During resection, the surgeon may use retractors to hold back the brain tissue to have better access to the tumor. The use of retractor causes additional deformation due to the applied forces, and therefore a new set of images and appropriate processing is necessary to maintain the accuracy of image guidance.

When the retractor is in the surgical field, it is usually not possible to use an ultrasound transducer to collect images. In this situation, stereovision is used to acquire surface data without contacting the brain. Specifically, to track displacements due to retraction, both pre- and post-retraction images need to be collected. The pre-retraction images can be from different surgical stages in different situations. In some cases, only iSV after post-dural opening is available, and therefore post-dural opening is used as the "pre-retraction" stage. In other cases, iSV surface is available immediately before the retractor is placed into the surgical field. Different strategies to simulate retraction are used for different situations; these retractor locations and effects are used 480 to update the mechanical model 480 for presence and location of that tool such that locations of tumor, surgical cavity, and other brain structures can be more precisely determined when mechanical modeling 468 is performed.

Retractor Modeling if iSV Surface Unavailable Immediately Before Retraction

Before the retractor is placed into the brain, the surgeon may have dissected along the surgical trajectory to split the tissue above the tumor. However, iSV may not be available in some cases immediately after incision, but only available after the retractor is in place. In this scenario, the "last-known-correct" stage is post-dural opening, and snapshot from the microscope can be used to simulate incision. To determine the 3D positions of landmarks in the microscope snapshot, it is first registered with the post-dural opening iSV image so that the outer boundary of the craniotomy aligns in two images. First, the location and depth of incision are determined by an incision plane (FIG. 13) and a focal plane, respectively. A set of points 752 at the incision location from a pre-incision or post-dural-opening 3D image pair are determined; these points are fitted into a plane to determine the incision plane 754 location of incision, the incision plane determined as perpendicular to the craniotomy. The focal plane 756 is then defined as a plane passing through the microscope focal point and parallel to the craniotomy when the microscope is focused at the bottom of cavity after retraction. The elements intersecting with the incision plane as well as the vertices (nodes) of the intersecting elements are then duplicated. Then the elements that were originally connected with these elements are found, and the connectivity is redefined to split the mesh. Finally, the duplicated nodes are considered as newly exposed craniotomy nodes, and boundary conditions at these nodes are revised accordingly Extracting Surface Sparse Data Using Simulated Retractor Planes In cases where iSV surface is not available immediately before the retractor is in place, sparse data are extracted using the following approach. First, the locations of retractors are identified from the image, and their 3D locations are fitted to two retractor planes and two polygons are defined to represent the width of each retractor. The centroids of the duplicated elements from the previous step are projected onto two retractor planes respectively, and only those that fall inside the polygons (within the width of the retractor) are kept. Two sets of displacement data are subsequently extracted based on the distance from the incision plane to each of the retractor planes.

Model Computation

Finally, a forward model scheme is applied to produce whole-brain deformation, so that the model results match the sparse data exactly to split the brain tissue. The corresponding uMR image stack is produced.

iSV Surface Available Immediately Before Retraction

If an iSV surface is available immediately after incision or partial resection but before the retractor is in place, the incision process can be treated as resection, and hence can be modeled using the approach described in the previous chapter, and a new set of MR images corresponding to the brain after incision is produced.

Tracking Retractor Movement Using of Algorithm

In cases where an iSV surface is available immediately before the retractor is placed into the field, an iSV sequence can be acquired to track the movement of the retractor. The ending iSV snapshot is reconstructed and compared with an iSV surface before retraction, to visualize the brain deformation.

The starting and ending snapshots from the sequence are registered to extract displacements due to use of the retractor and associated applied forces, which may shift additional portions of the exposed brain surface along the same direction.

The optical flow algorithm is used to track the movement of the retractor as well as the exposed brain surface. Then the starting and ending points of all displacement vectors are computed based on the iSV point clouds and displacements are transformed into 3D. The mechanical model is then run to determine an updated tumor location, and this location is prepared for presentation to the surgeon as, for example, an uMR tomographic image stack.

Calibration for 3-D Surface Extraction

Calibration of microscope position sensing and microscope viewing angles are as described in Hai Sun, for simplicity this calibration and tracking of microscope position will not be further elaborated here. Calibration of the stereo surface mapping and its operation are as described in patent application "Method and Apparatus for Calibration of Stereo-Optical Three-Dimensional Surface-Mapping System" number PCT/US13/20352 filed 4 Jan. 2013, and its parent documents, the contents of which are incorporated herein by reference.

Stereovision Calibration and Reconstruction

Figure 6:
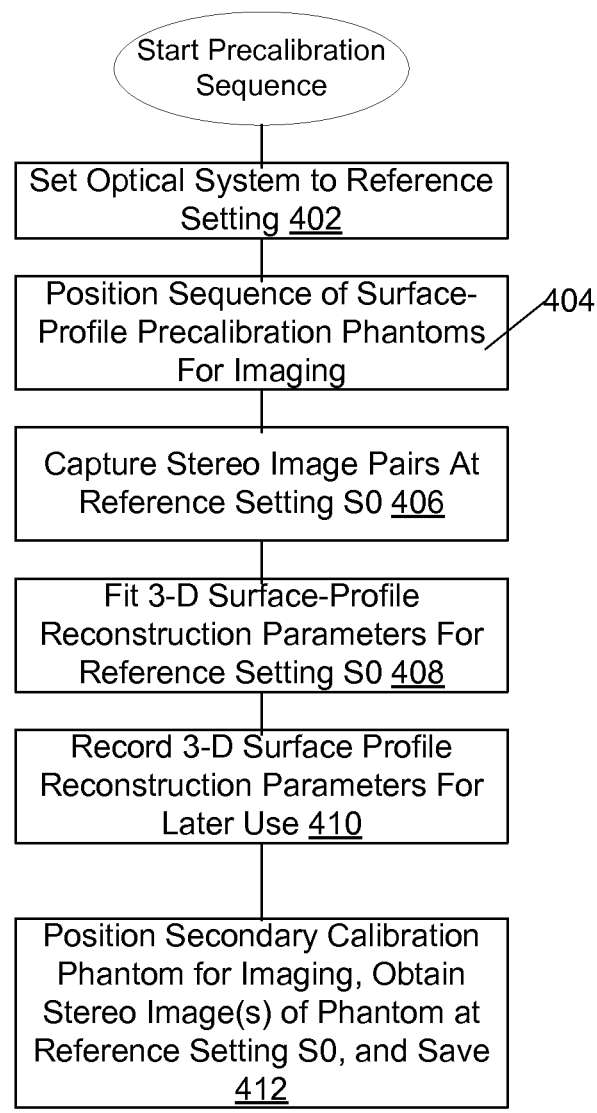
FIG. 6 is a flowchart of a precalibration procedure for determining a 3D surface map.
Figure 7:
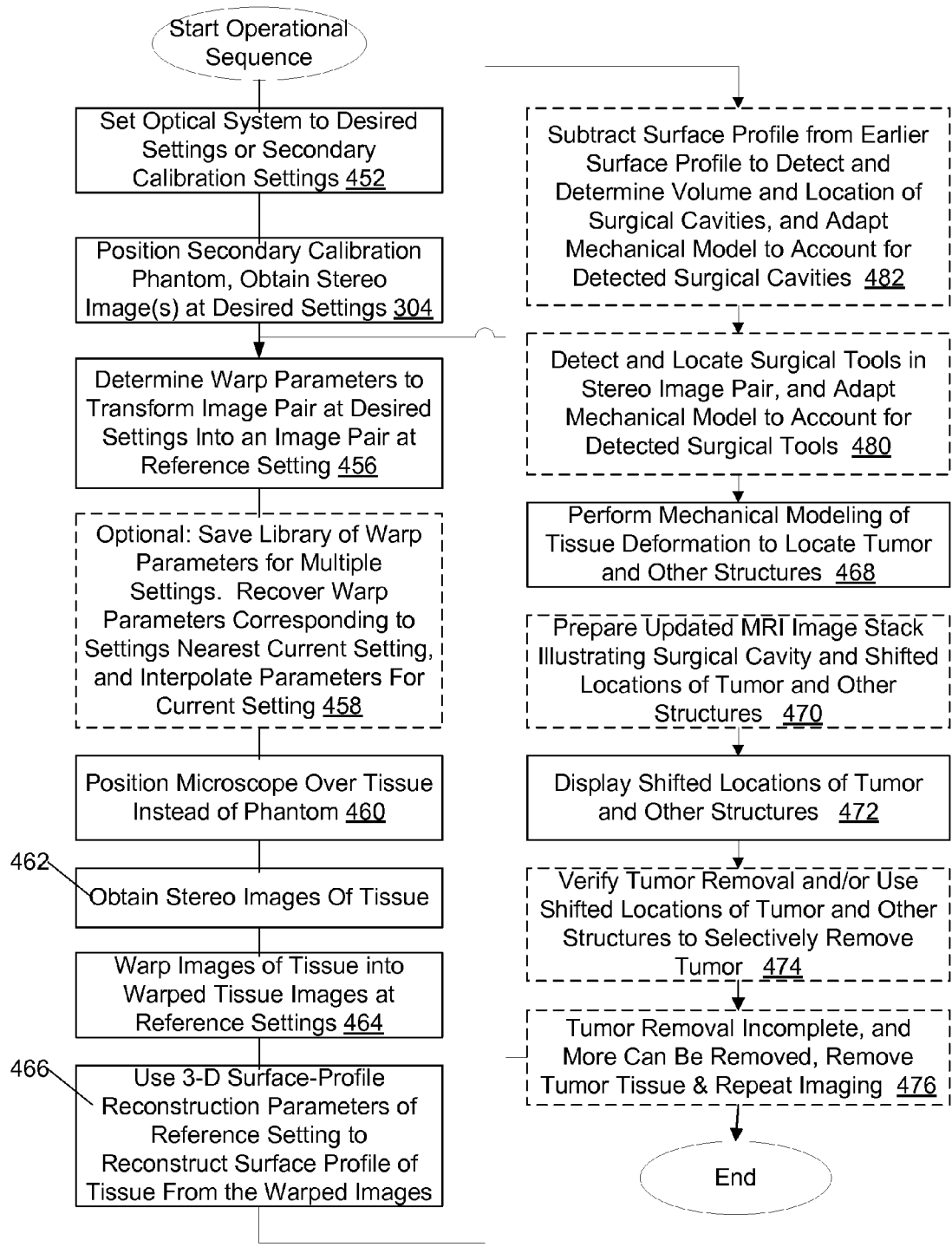
FIG. 7 is a flowchart of secondary calibration procedure for determining a 3D surface map, and modeling tumor location.

The surface profile extraction system uses a stereo optical system, such as that illustrated in FIG. 1 or 1A. With reference to FIG. 6, the optical system is set 402 to a reference setting S0 of a set of one or more reference settings. A sequence of optical precalibration phantoms are positioned 404 in view of the system, having known surface profiles, and parameters for reconstruction surface profile extraction routine 182 are derived that are sufficient for reconstructing a surface profile from a pair of stereo images taken with the optical system set 402 to the reference setting.

Techniques for stereo image calibration and reconstruction based on a pinhole camera model and radial lens distortion correction are outlined here for completeness, and are used in some embodiments. A 3D point in world space (X, Y, Z) is transformed into the camera image coordinates (x, y) using a perspective projection matrix:

$$\begin{pmatrix} x \\ y \\ 1 \end{pmatrix} = \begin{pmatrix} \alpha_x & 0 & C_x & 0 \\ 0 & \alpha_y & C_y & 0 \\ 0 & 0 & 1 & 0 \end{pmatrix} \times T \times \begin{pmatrix} X \\ Y \\ Z \\ 1 \end{pmatrix}, \qquad (1)$$

where $\alpha_x$ and $\alpha_y$ incorporate the perspective projection from camera to sensor coordinates and the transformation from sensor to image coordinates, $(C_x, C_y)$ is the image center, and T is a rigid body transformation describing the geometrical relationship of the effective optical centers between the views of the two cameras, 120, 122.

A precalibration phantom is prepared having reference marks at known positions in 3D space. A stereo pair of images is taken 406 of the precalibration phantom, assuming the precalibration phantom has known surface profile, providing a plurality of known points in three dimensions. A total of 11 camera parameters (6 extrinsic: 3 rotation and 3 translation; and 5 intrinsic: focal length, f, lens distortion parameter, k1, scale factor, Sx, and image center, (Cx, Cy)) are then determined through precalibration using a least squares fitting approach, and saved for later use as herein described. The intrinsic parameters include f focal length, κ• lens distortion coefficient, Sx non-square pixel scalar, Cx; Cy camera center. The extrinsic parameters include R(μx; μy; μz) rigid-body rotation, T(tx; ty; tz) rigid-body translation. Note that we now have a camera model that projects a point in the world to its image coordinates, the next step is to determine (i.e., calibrate) several unknown parameters among the equations presented above. In particular, the extrinsic camera parameters to be calibrated are the rotation and translation matrices (R; T) and the intrinsic parameters are the focal length (f), lens distortion coefficient •, scale factor (Sx), and image center (Cx; Cy).

The 3D precalibration phantoms have easily identified correspondence points or reference marks, where the correspondence points have known height relative to a phantom baseline. Each correspondence point should be identifiable in each of the images of the stereo pair.

Stereo image rectification is performed in a method similar to that of Hai Sun, pages 38-47.

Stereo image rectification is employed next to establish epipolar constraints that limit the search for correspondence points along "epipolar lines" (defined as the projection of the optical ray of one camera via the center of the other camera following a pinhole model). In addition, images are rotated so that pairs of epipolar lines are collinear and parallel to image raster lines in order to facilitate stereo matching. In an embodiment, an intensity-based correlation metric and a smoothness constraint aware used to find the correspondence points in both images of the pair. Each pair of correspondence points was is then transformed into their respective 3D camera space using the intrinsic parameters, and transformed into a common 3D space using the extrinsic parameters. Together with their respective camera centers in the common space, two optical rays were constructed with their intersection defining the 3D location of each of the correspondence point pair.

Since the 3D locations of the correspondence points are known on the precalibration phantoms, the parameters are fit 408 such that the extraction to a common 3D space gives results where extracted 3D points of an effective surface profile of the precalibration phantom match heights of the known points on the precalibration phantom. These 3D surface profile extraction parameters are then saved 410 for later use below.

Next, and not disclosed in Hai Sun, a secondary calibration phantom is positioned 412 in view of the optical system, and a stereo image pair of the runtime calibration phantom as viewed in the reference setting is captured and saved as part of calibration information. In an embodiment, the secondary calibration phantom is a two dimensional, flat, phantom having marks printed thereon. In an embodiment, the marks printed on the runtime calibration phantom are randomly generated squares of random intensities. In an alternative embodiment for use with cameras in aircraft or drones, the secondary calibration phantom is a particular, preselected, field or town. When it is desired to use the system to extract a surface profile of tissue 152, the optical system is set to an arbitrary runtime setting, typically having at least some optical system parameters, such as optical magnification, differing from those for the reference setting. The secondary calibration phantom may be used to calibrate warping parameters for the runtime setting, or may be used to calibrate warping parameters for secondary calibration points stored in a library or table as described below; a calibration for the arbitrary runtime setting determined by interpolation into the table and used for 3D surface extraction. Calibration of settings performed using the secondary calibration phantom, whether used for a runtime setting or for determining secondary calibration points, is described herein as secondary calibration.

Secondary Calibration

With the optical system set 452 to the arbitrary desired setting, the secondary calibration phantom is positioned in view of the optical system in a position approximating that where tissue 152 will be present during surgery, and a stereo image pair of the secondary calibration phantom is captured or taken 454 by cameras 120, 122 taken through the optical system with the optical system configured at secondary calibration setting S.

Next, deformation field parameters DFP for image warping routine 183 are derived 306 such that application of image warping routine 183 to the stereo image pair of the phantom with optical system at desired setting S provides a deformed stereo image pair that closely matches the stereo image pair of the secondary phantom as taken with the optical system in the reference setting S0.

The method for 3D surface extraction herein described warps stereo images captured using a desired setting S, using the deformation field obtained from images of a phantom at desired setting S and reference setting S0, into warped images corresponding to images taken at the reference setting S0. Because the reference setting S0 has been calibrated for surface extraction, the warped stereo images can then be used for surface reconstructing following the same calibration as determined for reference setting S0. The key to the technique is to find the equivalent image at a specific setting S0 that has been pre-calibrated for an image acquired at an arbitrary setting S.

Image Deformation due to the Change in Image Acquisition Settings and Target Surface Orientation To determine image deformation due to the change in image acquisition settings (i.e., m magnification and f focal length), in an experimental embodiment a series of phantom images were acquired using a planar secondary calibration phantom with randomly generated squares of random grayscale intensity by successively changing one parameter from its reference value while maintaining other optical system parameters at the corresponding reference value; in other embodiments other secondary calibration phantoms may be used. In an embodiment, the reference values of image magnification (m0) and focal length (f0) correspond to the lowest magnification and the shortest focal length that the microscope offers, respectively. Because image magnification alters the image acquired independently from the change in f or θ (which was verified with the deformation fields generated by changing m at different f and θ), only one set of images is necessary to determine an image deformation field due to the change in m (acquired with f0). With m0, image deformation due to the change in f was also determined by successively increasing f from f0. For these phantom images, the secondary calibration phantom was perpendicular to an optical axis centered between the effective optical axes of the two cameras.

Figure 8:
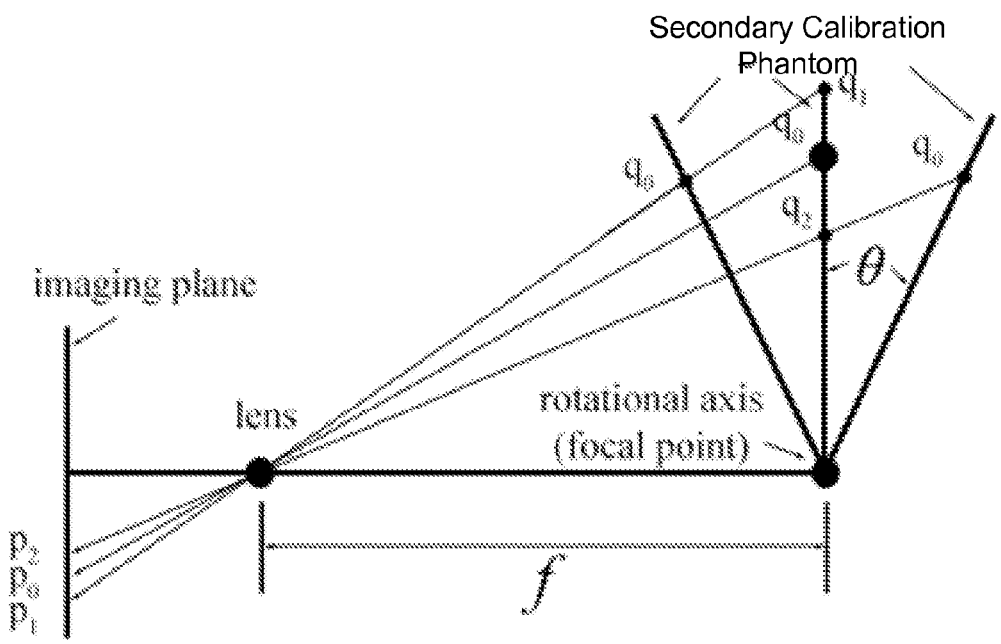
FIG. 8 is an illustration of secondary calibration
Figure 10:
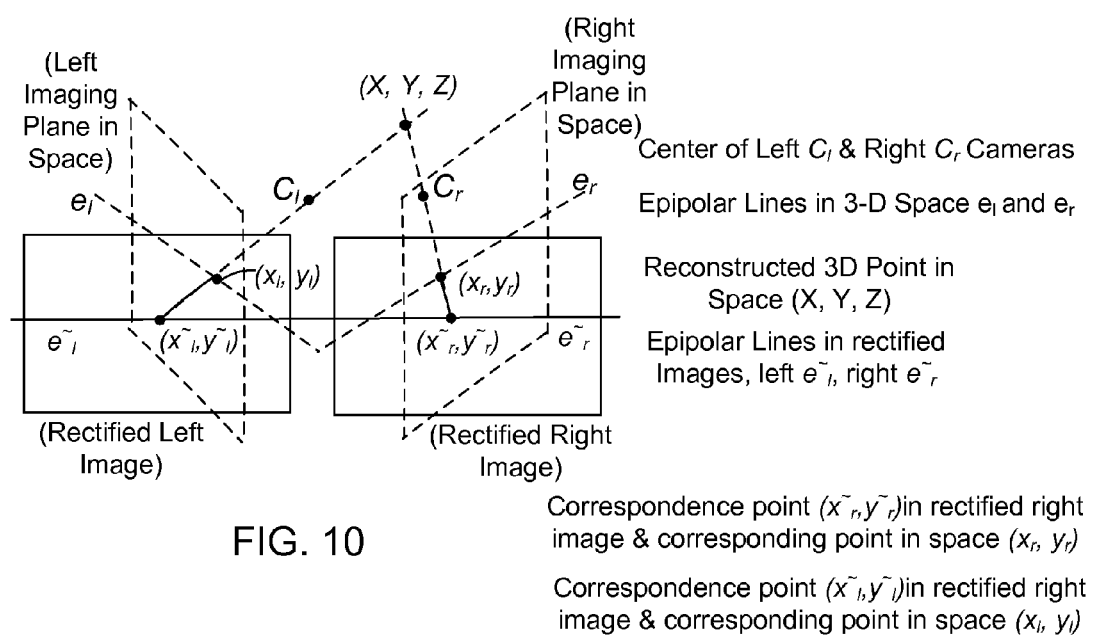
FIG. 10 is an illustration of surface reconstruction.

With reference to FIG. 8, in order to determine image deformation due to the change in θ, the pinhole camera model was employed. For arbitrary material points, q0 and qi initially on the secondary calibration phantom positioned at θ0, their corresponding image pixels, p0 and pi on the imaging plane, are co-linear with the pinhole camera lens. For a given material point, q0, its new pixel location when the target surface was rotated by θ, is given by the pixel location produced by the material point, qi on the original target surface (i.e., θ0), that intersects with the line segment generated by the pinhole lens and q0, as illustrated in FIG. 8. Image deformation due to the change is then produced by subtracting the two pixel locations, p1 and p0.

Based on the above description of generating image deformation fields due to the change in m, f, and θ, the following pseudo procedure outlines the sequence of phantom image acquisitions:

Set f=f0, and θ=θ0, successively increase m from m0 and acquire images for each setting of m;

Set m=m0 and θ=θ0, successively increase f from f0 and acquire images for each setting of f;

Set m=m0 and f=f0, successively increase θ from θ0, and acquire images for each setting of θ; verify that the predicted image deformation field based on pinhole camera model matched with measurement.

Image deformation due to the change in m and f are measured using the phantom images. By contrast, image deformation due to the change in θ is computed based on the pinhole camera model, and is verified using the phantom images.

Once appropriate warping parameters, such as a warping deformation field, is determined, the microscope is positioned 460 over tissue 152 instead of the phantom, and stereo images of the tissue are obtained 462 from the cameras 120, 122.

Image Warping to Reference Setting

Next, the stereo images of the tissue are warped 464 by optical warping routine 183 into equivalent images as if they had been taken at the reference settings.

A pseudo algorithm to warp images obtained at an arbitrary image acquisition setting (m, f) and surface orientation relative to the optical axis (θ):

1. Use deformation field due to the change in m to generate image at setting of (m0, f, θ);

2. Use the resulting image and analytical solution of deformation due to the change in θ, produce image at settings of (m0, f, θ0);

3. Use the resulting image and deformation field due to the change in f, to produce a warped image at the reference settings, (m0, f0, θ0);

In an alternative embodiment, a single deformation field, or warping parameters, for the entire transformation from the arbitrary setting (m, f, θ) into a warped image corresponding to an image as if it had been taken at the reference setting (m0, f0, θ0) is used in a single warping operation.

Next, the stereo precalibration parameters obtained from precalibration phantoms with the optical system at the reference setting (m0, f0, θ0) are used to reconstruct 466 a surface profile of the tissue in 3D. The reconstructed surface profile may then be used with a computer model of deformation 186 of the tissue and a pre-surgery location of a tumor or lesion as determined in three dimensions from pre-surgery images obtained by conventional medical imaging devices such as CT scanners and MRI machines to locate 468 the tumor 156 as displaced during surgery in a manner similar to that described by Hai Sun. Alternatively, or in addition to displaced tumor locations, the computer model of deformation of the tissue may be used to determine intra-surgery locations of other anatomic features of the tissue so that these features may be preserved.

Finally, image processor 180 uses a display system 190 to display the surface profile and tumor locations, or locations of other anatomic features, so that a surgeon may remove the tumor or lesion while preserving other critical anatomic features of the tissue. In an embodiment, an updated MRI (uMR) image stack is prepared 470 by warping or annotating the preoperative MRI to show the displaced locations of tumor and other structures. The determined displaced locations of tumor and other structures are displayed 472 to the surgeon, who may use this displayed information 474 to locate the tumor or additional tumor material for removal, or to determine whether the tumor has been successfully removed. If the tumor has not all been removed, more tumor may be removed and the process repeated 476 beginning with determining warping parameters for a current optical setting 456, in most embodiments by interpolating in table 458, and capturing a new stereo image pair 462 of the tissue.

Library-Based Calibrations

It can be inconvenient to require a surgeon to position a secondary calibration phantom in the field of view of a surgical microscope when the surgeon changes focal length, magnification, or other optical parameters of the system.

Figure 9:
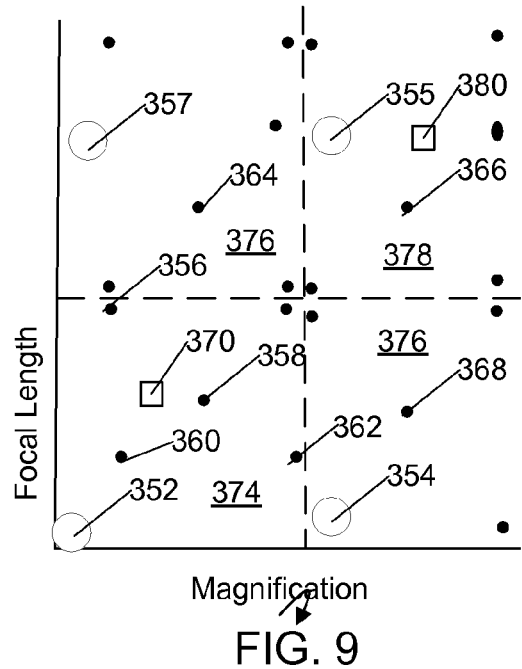
FIG. 9 illustrates points in a table or library of calibrations with primary and secondary calibration points

FIG. 9 illustrates a family of reference settings (including each reference setting S0) or primary calibration points 352, 354, together with secondary calibration points 356, 358, 360, 362, 364, 366, 368, are stored in a warp deformation field parameter (DFP(n)) and 3D reconstruction parameter multidimensional table or library 372 (FIG. 1). An encoder 374 is provided for the microscope zoom and focus controls. Table or library 372 is indexed by the zoom and focus control settings, which correspond to magnification and focal length. For simplicity, only magnification and focal length are illustrated in FIG. 9 in a two-dimensional diagram representative of a two-dimensional table, in an actual system additional optical parameters, such as microscope orientation angles θ, are provided as additional dimensions to the table. Each set of deformation field parameters is a constant representing no deformation for the primary calibration point S0 or points, or is derived by adjusting optical parameters of the system such as the image magnification (m) and focal length (f) parameters to correspond to the predetermined secondary calibration point, positioning the secondary calibration phantom, capturing an image pair is captured at this calibration point, and fitting of deformation parameters such that a warped image pair produced from the image pair closely resembles saved stereo images of the phantom captured at a reference setting S0, such as primary calibration point 352.

In this table-based embodiment, when surface profile extraction is desired at a runtime arbitrary optical setting set, such as setting 370, during surgery by a surgeon, the runtime optical settings are determined by determining the magnification m, and focal length f, using the encoder 374 on the zoom and focus controls. Angles are determined by reading microscope angle information from tracker 142. A deformation field parameter set for the runtime optical setting is then determined by interpolation from nearby entries in the table or library 372.

A runtime image pair of tissue is then captured. The runtime optical warping parameters are then used to warp the runtime image pair to an image pair that corresponds to the specific reference setting S0, 352 that was used for secondary calibration of the nearby entries in the table as heretofore described. 3D reconstruction is then performed using 3D reconstruction parameters determined for that specific reference setting.

The use of a reference setting S0 at the extreme low magnification end of the optical system zoom range, and at a nearest focus length of the optical system focus range, has advantage in that it can be reproducibly set as there is a mechanical stop at these points. Further, when an image is warped to correspond to a lower magnification setting, 3D reconstruction may be more accurately performed than when it warped to a higher magnification where portions of the warped image exceed the boundaries of images used to calibrate the 3D reconstruction parameters.

In an alternative embodiment, in order to provide more accurate 3D reconstruction at higher magnification and longer focal length settings, additional reference image acquisition settings at the midrange of optical system settings are used in addition to the extreme settings at the lowest magnification and shortest focal length. In this embodiment, additional reference settings 354, 355 are provided at a midrange of magnification. Further, in a particular embodiment, additional reference settings 355, 357 are provided at a reproducible, but greater than minimum, set-point of focal length. 3D reconstruction parameters are determined by primary calibration, similarly to the process heretofore described for determination of 3D reconstruction parameters for the reference setting S0, for each of these additional reference settings 354, 355, 357.

It is desirable that each reference setting S0, 352, 354, 355, 357 be a setting that the optical system can be reproducibly be returned to. Certain microscopes are provided with motorized focus and zoom controls, together with encoders 374. These microscopes may be provided with a preset or bookmark memory permitting them to be returned to a predetermined preset of focus and zoom; these microscopes are particularly adaptable for operation with more than one reference setting. Other microscopes may be equipped with a mechanical detent, such as a detent at a midpoint setting of magnification (or zoom). In embodiments using these optical systems, each reference setting S0, 352, 354, 355 is a setting that is bookmarked or at mechanical detents.

In a multiple-reference-setting embodiment, the plane of focal length and magnification, or in an embodiment having a single angle encoded a 3-space, or in an embodiment having two angles encoded a 4-space, is divided into quadrants, such as quadrant 374, 376, 378, cubes, or hypercubes (hereinafter quadrant) respectively.

In a multiple reference setting embodiment, secondary calibration points, such as calibration points 364, 366, and 368, are determined at multiple optical system settings in each quadrant, according to the procedure for secondary calibration described above, where each secondary calibration point provides distortion field parameters DFPs for warping an image taken at the calibration point to the primary calibration point of the quadrant within which the secondary calibration point lies. For example, in the illustration of FIG. 9, top right quadrant secondary calibration points 366 provide DFPs for warping images to correspond to images taken at the top right quadrant primary calibration point or reference setting 355; with bottom left quadrant secondary calibration points 356, 358, 360 provide DFPs for warping images to correspond to images taken at the bottom left quadrant primary calibration point or reference setting 352.

In the multiple-reference-setting embodiment, when a surgeon selects a runtime setting, such as setting 370, 380, the processor 124 uses the encoders 143 to determine the runtime setting. The processor 180 executes a selection routine to determine the quadrant in which the runtime setting occurs by comparing the runtime setting with settings of calibration points in the warp and 3D parameter table or library 372. Typically, the quadrant is chosen to be that having a reference setting, such as reference setting 352, 355 nearest in focal length to that of the runtime setting, and the nearest magnification setting less than the magnification of the runtime setting. A runtime distortion field parameter (DFP(run)) is then determined by interpolation, as heretofore described, between nearby secondary calibration points recorded in library 372.

As previously described, a runtime stereo image is then captured, and warped to correspond to images captured at the primary calibration point or reference setting, of that quadrant, such as setting 352 for the lower left quadrant 374 or setting 355 for runtime settings in the top right quadrant 378. 3D extraction is then performed on the warped image, using 3D extraction parameters recorded in library 372 and associated with the primary calibration point or reference setting 352, 355, associated with that quadrant.

Determining 3D Deformation Field

In an alternative embodiment, instead of determining specific correspondence points, determining 3D coordinates of those 3D correspondence points, and deriving a 3D surface map from a cloud of such points, a 3D image warping deformation field is determined that maps a first image, such as a left image, of each stereo pair into an image that corresponds to the second image, such as a right image, of the stereo pair. A 3-D surface map is then determined from that 3D image warping deformation field.

Image Reconstruction From Warping Field

Stereovision reconstruction can be expressed by the following equation to determine the 3D spatial coordinate, P, for a given sampling point in the rectified left image, p:

$$P=G(p,F(p))=G(p,p+u(p)), \tag{1A}$$

where F(p) is a functional form describing the image coordinate of the correspondence point of p in the rectified right image, and is obtained when the horizontal disparity, u(p), is available, and G is the geometrical operation (including transformation and triangulation) established from calibration. Therefore, reconstructing the 3D surface in space is reduced to establishing a disparity map between the two rectified images for a given set of calibration parameters. The quality (accuracy and density) and the computational efficiency of the disparity map determine overall performance in stereovision reconstruction. For purposes of this discussion, we refer to an unwarped left image and warp that image to correspond to a right image, however it is anticipated that left and right may be reversed in alternative embodiments. Establishing the disparity map between the rectified left ("undeformed") and right ("deformed") image pair is analogous to determining the motion field between the two images.

Determining a Vertically-Unconstrained 3D Warping Deformation Field

It is known that a particular point P(x, y, z) on a surface should appear along the same horizontal epipolar line $\bar{e}$ in each image of a stereo pair, although its location along that line will differ with the angle between the images and 3D height. In an embodiment, a 3D warping deformation field (3D-DFP) is determined by imposing a vertical, or epipolar, constraint while fitting deformation field parameters to the images. In a novel unconstrained embodiment, no such vertical constraint is imposed.

In the unconstrained embodiment, using a variational model and assuming the image intensity of a material point, (x, y), or its corresponding pixel does not change, a gray value constancy constraint $$I(p+w)=I(p), \tag{2}$$

is assumed in which p=(x, y) and the underlying flow field, w(p), is given by w(p)=(u(p), v(p)), where u(p) and v(p) are the horizontal and vertical components of the flow field, respectively. Global deviations from the gray value constancy assumption are measured by an energy term $$E_{Data}(u,v)=\int\psi(|I(p+w)-I(p)|^2)dp, \tag{3}$$

where a robust function, $\psi(x)=\sqrt{x^2+\epsilon^2}$, was used to enable an $L^1$ minimization in a particular study ($\epsilon$=0.001).

The gray value constancy constraint only applies locally and does not consider any interaction between neighboring pixels. Because the flow field in a natural scene is typically smooth, an additional piecewise smoothness constraint can be applied to the spatial domain, leading to the energy term $$E_{Smooth}(u,v) = \int \phi(|\nabla u|^2 + |\nabla v|^2) dp, \quad (4)$$

where $\phi$ is a robust function chosen to be identical to $\psi$, and $\nabla$ is the gradient operator where $$|\nabla(u)|^2 = u_x^2 + u_y^2 \left( u_x = \frac{\partial u}{\partial x}, u_y = \frac{\partial u}{\partial y} \right),$$

which is analogous for v.

Combining the gray value constancy and piecewise smoothness constraints leads to an objective function in the continuous spatial domain given by $$E(u,v) = E_{Data} + \alpha E_{Smooth}, \quad (5)$$

where $\alpha$ ($\alpha > 0$; empirically chosen as 0.02 in a particular feasibility study) is a regularization parameter. Computing the optical flow is then transformed into an optimization problem to determine the spatially continuous flow field (defined by u and v) that minimizes the total energy, E. In this study, an iterative reweighted least squares algorithm, and a multi-scale approach starting with a coarse, smoothed image set were used to ensure global minimization.

Disparity Estimation Based on Optical Flow

In a particular flow-based stereo surface reconstruction study performed on intraoperative stereo pairs taken during surgical procedures, the rectified images were down-sampled to expedite processing, with sufficient resolution retained to provide adequate 3D modeling. The full-field horizontal displacements from two-frame optical flow on the two (down-sampled) rectified images served as the disparity map, u(p), from which texture-encoded 3D stereo surface is readily reconstructed from the geometrical operations defined above. Although the flow field is spatially smooth due to the smoothness constraint applied to the optimization, spurious disparities can still occur in regions of insufficient features and/or with occluded pixels, similarly to SSD-based correspondence matching. Instead of correcting for these spurious disparities in the solution field by applying appropriate constraints in optimization with additional burden in algorithmic implementation and increase in computational cost, we detect regions of spurious disparities using values of the vertical flow field, v(p). This strategy was possible because ground-truth values of zeros for v(p) were known a priori as a direct result of the epipolar constraint where correspondence point pairs were pre-aligned on the same horizontal lines in rectified images.

Therefore, pixels with large absolute values of vertical discrepancy v(p) (such as pixels displaced above or below a certain threshold) that violate the epipolar constraint also indicate likely spurious horizontal disparities in the flow field, u(p). In some embodiments these pixels are simply excluded from stereo surface reconstruction. In an alternative embodiment, the sampling pixels are empirically filtered into regions of high, mid, or low confidence levels based on the absolute vertical disparities, abs (v), when they were either less than a first threshold, between the first threshold and a second threshold, or above the second threshold in pixels, respectively, where these particular threshold values were empirically chosen. Horizontal disparity values for pixels with a high or low confidence level were either retained or removed, while those in-between were interpolated based on those of a high confidence level. Such a two-tier threshold interpolation/exclusion scheme was effective in maximizing regions of sufficient disparity accuracies while excluding from surface reconstruction those with insufficient features such as those due to specular artifacts or occluded pixels.

An experimental embodiment using 3D reconstruction based upon optical flow using a vertically unconstrained image deformation fitting process and using vertical disparity for disparity detection provided superior surface reconstruction, and may permit more accurate determination of intraoperative tumor locations.

Interpolation, Warp to Reference, Warp to 3D, Model Movement

Figure 11:
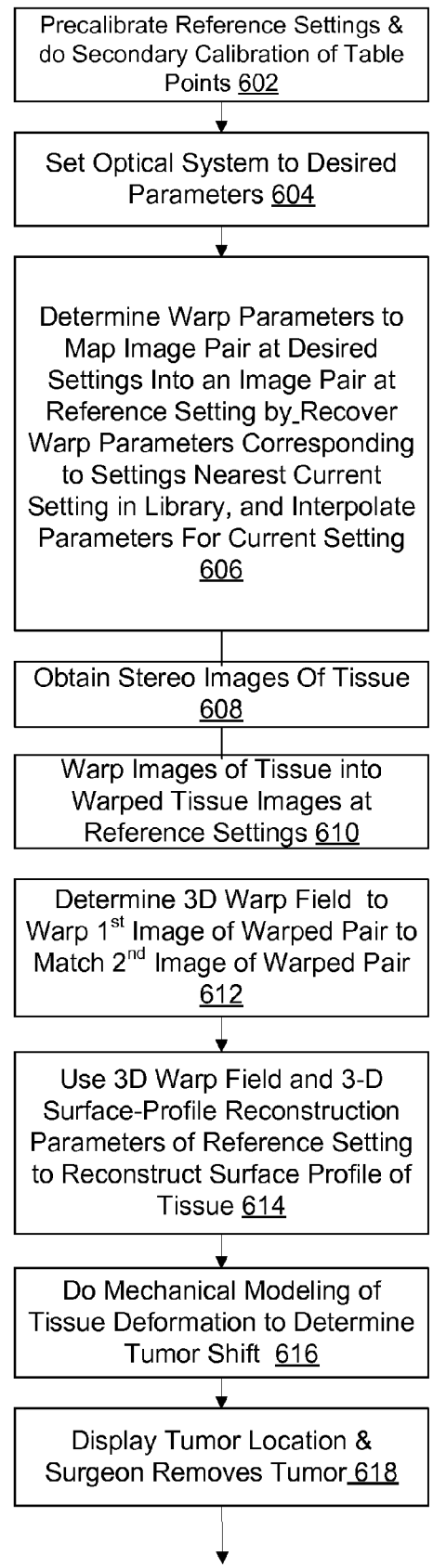
FIG. 11 is a flowchart illustrating modeling tumor shift using a combination of methods herein described.

Putting together the heretofore described procedures, as illustrated in FIG. 11, a calibration library or table 372 is prepared 602 by doing primary calibration using the 3D calibration phantoms at one or more reference settings, and 3D reconstruction parameters are stored for each setting. Secondary calibration points are then added into the table 372 by imaging a secondary calibration phantom at each reference setting, setting the optical system to correspond to each secondary calibration point, re-imaging the secondary calibration phantom, and determining warp field parameters that map the re-image of the secondary calibration phantom to match the image taken at a reference setting appropriate for use with that secondary calibration point; these warp field parameters are stored in the table.

The optical system is then set to a desired setting 604, and warp field parameters suitable for mapping images taken at the desired setting into warped images corresponding to images taken at a reference setting are determined 606 by reading warp parameters for secondary calibration points near the desired setting and interpolating to give interpolated warp parameters. A stereo image pair is obtained 608 from the cameras and the interpolated warp parameters are used to warp 610 that image pair to a warped image pair that corresponds to an image pair taken at the reference setting used for calibrating those secondary calibration points.

A vertically-unconstrained warp-field fitting operation is then performed to determine 612 3D warp field parameters for warping a first image of the warped stereo image into a second image of the warped stereo image pair, and, where vertical deformation in the warp field exceeds a first limit, the warp field is adjusted, and where vertical deformation exceeds a second limit, associated image pixels are excluded from consideration in the warp-field fitting operation in a further iteration of fitting the 3D warp field parameters to the warped image pair.

The fitted 3D warp field parameters are used to reconstruct 614 a surface profile of the tissue. This surface profile is in turn used to constrain a mechanical model of the tissue, the model is used to determine shift of structures in the tissue, such as a shift of a tumor 616, and an intraoperative location of those structures and the tumor. The intraoperative structure locations and tumor location is then displayed 618 such that a surgeon can remove the tumor.

The heretofore described procedure may be used to determine intraoperative positions of a lesion or other structures in tissue of the mammalian, including human brain or may be adapted to determining intraoperative positions in other soft-tissue organs.

Combinations

Many combinations of features herein described are anticipated as possible, in particular the following combinations are anticipated:

In an embodiment, a method designated A wherein the intraoperative stereovision surface mapping selected from the group consisting of a surface map derived from a point cloud determined from triangulation and a surface map derived from intraoperative stereovision derived using an image warping field determined to map one image of a stereo image pair into another image of the stereo image pair; a calibration selected from a conventionally calibration using three dimensional phantoms at the same optical system setting as used for the stereovision surface mapping, a calibration determined at a reference setting to which stereo image pairs are warped prior to using calibration information to extract a 3D surface map from the stereo image pairs, and a table-based calibration where warping parameters for warping stereo image pairs to a reference setting are determined by interpolation in a table, the image pairs being warped to warped image pairs corresponding to images taken at the reference setting prior to using calibration information to extract a 3D surface map from the warped stereo image pairs; the intraoperative stereovision surface map then used with or without supplemental intraoperative ultrasound information to model deformation of an organ, which in a particular embodiment is brain, to determine shift of tumor and/or other structures of the organ thereby giving intraoperative locations of the tumor and/or other structures; the intraoperative locations then being displayed.

An embodiment designated AA including the embodiment designated A, the method further including extraction of surgical cavity volume and location, and/or surgical instrument presence and location, and wherein the model of deformation of the organ is adapted to model the surgical cavity and/or surgical instrument to account for effects of the cavity and/or instrument in determining intraoperative locations of tumor and/or other structures.

A method designated AB including the embodiment designated A or AA, wherein the surface map is derived using an image warping field determined to map one image of a stereo image pair into another image of the stereo image pair, the image warping field determined by vertically unconstrained fitting.

A method designated AC including the method designated A, AA, or AB and further including one or both of extracting a 3 dimensional representation of a surgical cavity, wherein the mechanical model of tissue is adapted with the 3-dimensional model of the surgical cavity such that the cavity is taken into account in determining displacement of the particular structure in the tissue; and locating a surgical tool, wherein the mechanical model of tissue is adapted with a location of the surgical tool such that presence and location of the tool is taken into account in determining displacement of the particular structure in the tissue.

A system comprising an optical system having a plurality of settings, an image processor, and a display subsystem, the system configured to perform the method designated A, AA, or AB.

A method designated B for determining a 3D model of a surface includes calibrating 3D reconstruction parameters for at least one reference setting of an optical system; calibrating image warping parameters for at least one secondary calibration point settings, the image warping parameters adapted to control an image warping routine to warp images taken at that secondary calibration point setting into warped images corresponding to images taken at the reference setting; taking an stereo image through the optical system with the optical system at a current setting; determining warping parameters from the image warping parameters for at least one secondary calibration setting of the at least one secondary calibration settings, the warping parameters for warping the stereo image taken at the current setting into a warped stereo image corresponding to a stereo image taken at the reference setting; warping the stereo image into the warped stereo image; determining three-dimensional (3D) warping parameters for warping a first image of the warped stereo image into a second image of the stereo image; and using the 3D warping parameters for determining the 3D model of the surface.

A method designated BA including the method designated B wherein there are image warping parameters for more than one secondary calibration point setting stored in a table, and wherein the step of determining warping parameters from the image warping parameters for at least one secondary calibration point setting includes interpolating between image warping parameters stored in the table.

A method designated BB including the method designated B or BA wherein the step of determining 3D warping parameters uses vertically unconstrained fitting, and wherein pixels initially having vertical warp parameters exceeding a threshold are excluded from fitting the 3D warping parameters.

A method designated BC including the method designated BB or BA and further including using the 3D model of the surface to constrain a mechanical model of tissue to determine a displacement of a particular structure in the tissue.

A method designated BD including the method designated BC and further including extracting a 3 dimensional representation of a surgical cavity, and wherein the mechanical model of tissue is adapted with the 3-dimensional model of the surgical cavity such that the cavity is taken into account in determining displacement of the particular structure in the tissue.

A method designated BDA, including the method designated BD, wherein the 3-dimensional representation of a surgical cavity is determined by projecting a pre-resection 3D model of the surface onto a plane as a first projection, projecting a post-resection model of the surface onto the same plane as a second projection, determining an image-warping that maps the first projection into the second projection or the second projection into the first projection, this mapping is used with the pre-resection and post-resection models of the surface to determine a 3-dimensional model of difference, and the 3-dimensional representation of the surgical cavity is derived from the 3-dimensional model of difference.

A method designated BE including the method designated BC or BD and further including further comprising locating a surgical tool, and wherein the mechanical model of tissue is adapted with a location of the surgical tool such that presence and location of the tool is taken into account in determining displacement of the particular structure in the tissue.

A system designated C for determining a 3D model of a surface including an optical system having a plurality of settings, each setting providing a specific focal length and magnification, the optical system comprising an encoder for observing a current setting of the optical system; a memory configured to contain calibrated 3D reconstruction parameters for at least one reference setting of the optical system; the memory further configured with image warping parameters for at least one secondary calibration setting, the image warping parameters adapted to control an image warping routine to warp images taken at that secondary calibration setting into warped images corresponding to images taken at a reference setting of the at least one reference setting; a camera coupled to capture stereo images through the optical system; a processor configured with machine readable instructions in the memory, the machine readable instructions comprising instructions for determining warping parameters from the image warping parameters for at least one secondary calibration point, the warping parameters for warping the stereo image into a warped stereo image corresponding to a stereo image taken at the reference point; the memory further configured with machine readable instructions for warping the stereo image into the warped stereo image; the memory further configured with machine readable instructions for determining three-dimensional (3D) warping parameters for warping a first image of the warped stereo image into a second image of the stereo image; the memory further configured with machine readable instructions for using the 3D warping parameters for determining the 3D model of the surface.

A system designated CA including the system designated C wherein the memory is configured with image warping parameters for more than one secondary calibration setting stored in a table, and wherein the machine readable instructions for determining warping parameters from the image warping parameters for at least one secondary calibration point includes instructions for interpolating between image warping parameters stored in the table.

A system designated CB including the system designated C or CA wherein the machine readable instructions for determining 3D warping parameters include instructions for performing vertically unconstrained fitting, and wherein pixels initially having vertical warp parameters exceeding a threshold are excluded from fitting the 3D warping parameters.

A method designated D for determining intraoperative location of a lesion in mammalian tissue of an organ from preoperative imaging including determining a three dimensional location of the lesion in preoperative images; determining three dimensional locations of surface features of the organ in the preoperative images; determining a preoperative surface map of the organ; determining an intraoperative three dimensional surface map of the organ incorporating locations of the surface features; determining three dimensional displacements of the surface features between their positions in preoperative images and their positions in the intraoperative three dimensional surface map of the organ; constraining a computer based model of deformation of the organ with both the intraoperative three dimensional surface map and the three dimensional displacements of the surface features; and applying the computer based model of deformation to determine intraoperative locations of the lesion.

A method designated DA including the method designated D further including determining preoperative locations of additional structures of the organ; and applying the computer based model of deformation to determine intraoperative locations of the additional structures of the organ.

A method designated DB including the method designated DA further including extracting a 3 dimensional representation of a surgical cavity, and wherein the mechanical model of tissue is adapted with the 3-dimensional model of the surgical cavity such that the cavity is taken into account in determining displacement of the particular structure in the tissue.

A method designated DBA, including the method designated DB, wherein the 3-dimensional representation of a surgical cavity is determined by projecting a pre-resection 3D model of the surface onto a plane as a first projection, projecting a post-resection model of the surface onto the same plane as a second projection, determining an image-warping that maps the first projection into the second projection or the second projection into the first projection, this mapping is used with the pre-resection and post-resection models of the surface to determine a 3-dimensional model of difference, and the 3-dimensional representation of the surgical cavity is derived from the 3-dimensional model of difference.

A method designated DC including the method designated DA or DB and further including locating a surgical tool, and wherein the mechanical model of tissue is adapted with a location of the surgical tool such that presence and location of the tool is taken into account in determining displacement of the particular structure in the tissue.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A method for determining a 3D model of a surface comprising:
    calibrating 3D reconstruction parameters for at least one reference setting of an optical system;
    calibrating image warping parameters for at least one secondary calibration settings, the image warping parameters adapted to control an image warping routine to warp images taken at that secondary calibration setting into warped images corresponding to images taken at the reference setting;
    taking an observed stereo image through the optical system with the optical system at a current setting;
    determining warping parameters from the image warping parameters for at least one secondary calibration setting of the at least one secondary calibration settings, the warping parameters for warping the observed stereo image taken through the optical system with the optical system at the current setting into a warped stereo image corresponding to a stereo image taken at the reference setting;
    warping the observed stereo image at the current setting into the warped stereo image corresponding to a stereo image taken at the reference setting;
    determining three-dimensional (3D) warping parameters for warping a first image of the warped stereo image corresponding to a stereo image taken at the reference setting into a second image of the warped stereo image corresponding to a stereo image taken at the reference setting; and
    using the 3D warping parameters to determine the 3D model of the surface.

2. The method of claim 1 wherein there are image warping parameters for more than one secondary calibration setting stored in a table, and wherein the step of determining warping parameters from the image warping parameters for at least one secondary calibration setting includes interpolating between image warping parameters stored in the table.

3. The method of claim 2 wherein the step of determining 3D warping parameters uses vertically unconstrained fitting, and wherein pixels initially having vertical warp parameters exceeding a threshold are excluded from fitting the 3D warping parameters.

4. The method of claim 3 further comprising using the 3D model of the surface to constrain a mechanical model of tissue to determine a displacement of a particular structure in the tissue.

5. The method of claim 4 further comprising extracting a 3 dimensional representation of a surgical cavity, and wherein the mechanical model of tissue is adapted with the 3-dimensional model of the surgical cavity such that the cavity is taken into account in determining displacement of the particular structure in the tissue; wherein the 3-dimensional representation of a surgical cavity is determined by projecting a pre-resection 3D model of the surface onto a plane as a first projection, projecting a post-resection model of the surface onto the same plane as a second projection, determining an image-warping that maps the first projection into the second projection or the second projection into the first projection, this mapping is used with the pre-resection and post-resection models of the surface to determine a 3-dimensional model of difference, and the 3-dimensional representation of the surgical cavity is derived from the 3-dimensional model of difference.

6. The method of claim 4 further comprising locating a surgical tool, and wherein the mechanical model of tissue is adapted with a location of the surgical tool such that presence and location of the tool is taken into account in determining displacement of the particular structure in the tissue.

7. The method of claim 1 wherein the step of determining 3D warping parameters uses vertically unconstrained fitting, and wherein pixels initially having vertical warp parameters exceeding a threshold are excluded from fitting the 3D warping parameters.

8. The method of claim 7 further comprising using the 3D model of the surface to constrain a mechanical model of tissue to determine a displacement of a particular structure in the tissue.

9. The method of claim 8 further comprising extracting a 3 dimensional representation of a surgical cavity, and wherein the mechanical model of tissue is adapted with the 3-dimensional model of the surgical cavity such that the cavity is taken into account in determining displacement of the particular structure in the tissue; wherein the 3-dimensional representation of a surgical cavity is determined by projecting a pre-resection 3D model of the surface onto a plane as a first projection, projecting a post-resection model of the surface onto the same plane as a second projection, determining an image-warping that maps the first projection into the second projection or the second projection into the first projection, this mapping is used with the pre-resection and post-resection models of the surface to determine a 3-dimensional model of difference, and the 3-dimensional representation of the surgical cavity is derived from the 3-dimensional model of difference.

10. The method of claim 9 further comprising locating a surgical tool, and wherein the mechanical model of tissue is adapted with a location of the surgical tool such that presence and location of the tool is taken into account in determining displacement of the particular structure in the tissue.

11. A system for determining a 3D model of a surface comprising:
an optical system having a plurality of settings, each setting providing a specific focal length and magnification, the optical system comprising an encoder for observing a current setting of the optical system;
a memory configured to contain calibrated 3D reconstruction parameters for at least one reference setting of the optical system;
the memory further configured with image warping parameters for at least one secondary calibration setting, the image warping parameters adapted to control an image warping routine to warp images taken at that secondary calibration setting into warped images corresponding to images taken at a reference setting of the at least one reference setting;
a camera coupled to capture an observed stereo image through the optical system at a current setting;
a processor configured with machine readable instructions in the memory, the machine readable instructions comprising instructions for determining warping parameters from the current setting and image warping parameters for at least one secondary calibration setting, the warping parameters being warping parameters adapted for warping the observed stereo image into a warped stereo image corresponding to a stereo image taken at the reference setting;
the memory further configured with machine readable instructions for warping the observed stereo image into the warped stereo image corresponding to a stereo image taken at the reference setting;
the memory further configured with machine readable instructions for determining three-dimensional (3D) warping parameters for warping a first image of the warped stereo image corresponding to a stereo image taken at the reference setting into a second image of the stereo image corresponding to a stereo image taken at the reference setting;
the memory further configured with machine readable instructions for using the 3D warping parameters for determining the 3D model of the surface.

12. The system of claim 11 wherein the memory is configured with image warping parameters for more than one secondary calibration setting stored in a table, and wherein the machine readable instructions for determining warping parameters from the image warping parameters for at least one secondary calibration setting includes instructions for interpolating between image warping parameters stored in the table.

13. The system of claim 12 wherein the machine readable instructions for determining 3D warping parameters include instructions for performing vertically unconstrained fitting, and wherein pixels initially having vertical warp parameters exceeding a threshold are excluded from fitting the 3D warping parameters.

14. The system of claim 13 further comprising extracting a 3 dimensional representation of a surgical cavity, and wherein the mechanical model of tissue is adapted with the 3-dimensional model of the surgical cavity such that the cavity is taken into account in determining displacement of the particular structure in the tissue.

15. The system of claim 13 further comprising locating a surgical tool, and wherein the mechanical model of tissue is adapted with a location of the surgical tool such that presence and location of the tool is taken into account in determining displacement of the particular structure in the tissue.

16. The system of claim 12 wherein the machine readable instructions for determining 3D warping parameters include instructions for performing vertically unconstrained fitting, and wherein pixels initially having vertical warp parameters exceeding a threshold are excluded from fitting the 3D warping parameters.

17. The system of claim 16 further comprising extracting a 3 dimensional representation of a surgical cavity, and wherein the mechanical model of tissue is adapted with the 3-dimensional model of the surgical cavity such that the cavity is taken into account in determining displacement of the particular structure in the tissue.

18. The system of claim 17 further comprising locating a surgical tool, and wherein the mechanical model of tissue is adapted with a location of the surgical tool such that presence and location of the tool is taken into account in determining displacement of the particular structure in the tissue.

* * * * *